US008600100B2

(12) United States Patent
Hill

(10) Patent No.: US 8,600,100 B2
(45) Date of Patent: Dec. 3, 2013

(54) METHOD OF ASSESSING PEOPLE'S SELF-PRESENTATION AND ACTIONS TO EVALUATE PERSONALITY TYPE, BEHAVIORAL TENDENCIES, CREDIBILITY, MOTIVATIONS AND OTHER INSIGHTS THROUGH FACIAL MUSCLE ACTIVITY AND EXPRESSIONS

(75) Inventor: Daniel A. Hill, St. Paul, MN (US)

(73) Assignee: Sensory Logic, Inc., Minneapolis, MN (US)

( * ) Notice: Subject to any disclaimer, the term of this patent is extended or adjusted under 35 U.S.C. 154(b) by 774 days.

(21) Appl. No.: 12/762,076

(22) Filed: Apr. 16, 2010

(65) Prior Publication Data

US 2010/0266213 A1    Oct. 21, 2010

Related U.S. Application Data

(60) Provisional application No. 61/169,806, filed on Apr. 16, 2009.

(51) Int. Cl.
*G06K 9/00* (2006.01)

(52) U.S. Cl.
USPC ........................... 382/100; 382/118; 434/236

(58) Field of Classification Search
USPC .................................. 382/100, 118; 434/236
See application file for complete search history.

(56) References Cited

U.S. PATENT DOCUMENTS

| | | |
|---|---|---|
| 3,034,500 A | 5/1962 | Backster, Jr. |
| 3,548,806 A | 12/1970 | Fisher |
| 3,870,034 A | 3/1975 | James |
| 4,448,203 A | 5/1984 | Williamson et al. |
| 4,627,818 A | 12/1986 | Von Fellenberg |
| 4,794,533 A | 12/1988 | Cohen |

(Continued)

FOREIGN PATENT DOCUMENTS

| | | |
|---|---|---|
| EP | 1678660 A1 | 7/2006 |
| JP | 08115367 A | 5/1996 |
| WO | WO 02/087443 A1 | 11/2002 |
| WO | WO 2004/091371 A2 | 11/2004 |

OTHER PUBLICATIONS

Zhang et al. "Active and Dynamic Information Fusion for Facial Expression Understanding from Image Sequences." IEEE Transactions on Pattern Analysis and Machine Intelligence, vol. 27, No. 5, May 2005, pp. 699-714.*

(Continued)

*Primary Examiner* — Jon Chang
(74) *Attorney, Agent, or Firm* — Schwegman Lundberg & Woessner, P.A.

(57) ABSTRACT

A method of assessing an individual through facial muscle activity and expressions includes receiving a visual recording stored on a computer-readable medium of an individual's non-verbal responses to a stimulus, the non-verbal response comprising facial expressions of the individual. The recording is accessed to automatically detect and record expressional repositioning of each of a plurality of selected facial features by conducting a computerized comparison of the facial position of each selected facial feature through sequential facial images. The contemporaneously detected and recorded expressional repositionings are automatically coded to an action unit, a combination of action units, and/or at least one emotion. The action unit, combination of action units, and/or at least one emotion are analyzed to assess one or more characteristics of the individual to develop a profile of the individual's personality in relation to the objective for which the individual is being assessed.

28 Claims, 19 Drawing Sheets

(56) References Cited

U.S. PATENT DOCUMENTS

| | | | |
|---|---|---|---|
| 4,807,642 | A | 2/1989 | Brown |
| 4,817,628 | A | 4/1989 | Zealer et al. |
| 4,859,050 | A | 8/1989 | Borah et al. |
| 4,964,411 | A | 10/1990 | Johnson et al. |
| 4,975,960 | A | 12/1990 | Petajan |
| 5,031,228 | A | 7/1991 | Lu |
| 5,084,819 | A | 1/1992 | Dewey et al. |
| 5,092,343 | A | 3/1992 | Spitzer et al. |
| 5,124,911 | A | 6/1992 | Sack |
| 5,148,477 | A | 9/1992 | Neely et al. |
| 5,164,992 | A | 11/1992 | Turk et al. |
| 5,219,322 | A | 6/1993 | Weathers |
| 5,247,938 | A | 9/1993 | Silverstein et al. |
| 5,436,830 | A | 7/1995 | Zaltman |
| 5,607,186 | A | 3/1997 | Schroeder et al. |
| 5,663,900 | A | 9/1997 | Bhandari et al. |
| 5,676,138 | A | 10/1997 | Zawilinski |
| 5,710,833 | A | 1/1998 | Moghaddam et al. |
| 5,725,472 | A | 3/1998 | Weathers |
| 5,741,217 | A | 4/1998 | Gero |
| 5,772,591 | A | 6/1998 | Cram |
| 5,774,357 | A | 6/1998 | Hoffberg et al. |
| 5,774,591 | A | 6/1998 | Black et al. |
| 5,802,208 | A | 9/1998 | Podilchuk et al. |
| 5,802,220 | A | 9/1998 | Black et al. |
| 5,871,211 | A | 2/1999 | Was |
| 5,875,108 | A | 2/1999 | Hoffberg et al. |
| 5,901,244 | A | 5/1999 | Souma et al. |
| 6,004,312 | A | 12/1999 | Finneran et al. |
| 6,008,817 | A | 12/1999 | Gilmore, Jr. |
| 6,009,210 | A | 12/1999 | Kang |
| 6,026,321 | A | 2/2000 | Miyata et al. |
| 6,026,322 | A | 2/2000 | Korenman et al. |
| 6,088,040 | A | 7/2000 | Oda et al. |
| 6,099,319 | A | 8/2000 | Zaltman et al. |
| 6,185,534 | B1 | 2/2001 | Breese et al. |
| 6,292,575 | B1 | 9/2001 | Bortolussi et al. |
| 6,309,342 | B1 | 10/2001 | Blazey et al. |
| 6,311,190 | B1 | 10/2001 | Bayer et al. |
| 6,345,109 | B1 | 2/2002 | Souma et al. |
| 6,422,999 | B1 | 7/2002 | Hill |
| 6,443,840 | B2 | 9/2002 | Von Kohorn |
| 6,453,194 | B1 | 9/2002 | Hill |
| 6,533,583 | B1 | 3/2003 | Sportelli |
| 6,611,613 | B1 | 8/2003 | Kang et al. |
| 6,681,032 | B2 | 1/2004 | Bortolussi et al. |
| 6,879,709 | B2 | 4/2005 | Tian et al. |
| 7,003,139 | B2 | 2/2006 | Endrikhovski et al. |
| 7,113,916 | B1 | 9/2006 | Hill |
| 7,120,880 | B1 | 10/2006 | Dryer et al. |
| 7,233,684 | B2 | 6/2007 | Fedorovskaya et al. |
| 7,246,081 | B2 | 7/2007 | Hill |
| 7,388,971 | B2 * | 6/2008 | Rice et al. ............ 382/118 |
| 2002/0108125 | A1 | 8/2002 | Joao |
| 2003/0133599 | A1 | 7/2003 | Tian et al. |
| 2003/0156304 | A1 | 8/2003 | Fedorovskaya et al. |
| 2003/0165269 | A1 | 9/2003 | Fedorovskaya et al. |
| 2003/0165270 | A1 | 9/2003 | Endrikhovski et al. |
| 2004/0101212 | A1 | 5/2004 | Fedorovskaya et al. |
| 2005/0079474 | A1 | 4/2005 | Lowe |
| 2006/0047515 | A1 | 3/2006 | Connors |
| 2007/0066916 | A1 | 3/2007 | Lemos |
| 2008/0026212 | A1 | 1/2008 | Fujii |
| 2008/0052080 | A1 | 2/2008 | Narayanan |
| 2008/0260212 | A1 * | 10/2008 | Moskal et al. ........ 382/118 |
| 2009/0285456 | A1 * | 11/2009 | Moon et al. .......... 382/118 |
| 2012/0002848 | A1 | 1/2012 | Hill |

OTHER PUBLICATIONS

Cowell et al. "Extracting Subtle Facial Expression for Emotional Analysis." IEEE International Conference on Systems, Man and Cybernetics, vol. 1, 2004, pp. 677-681.*

Ryan et al. "Automated Facial Expression Recognition System." 43rd Annual 2009 Internal Carnahan Conference on Security Technology, Oct. 5, 2009, pp. 172-177.*

Hill, Daniel A.; "Facial Coding Analysis—Chapter 10"; Sensory Logic, Inc., 2002, pp. 151-179.

Bartlett, M.S., et al., "Measuring facial expressions by computer image analysis", Psychophysicology, 36 (1999), p. 253-263. Cambridge University Press.

Bassili, JN., "Emotion recognition: the role of facial movement and the relative importance of upper and lower areas of the face", Journal of Personality and Social Psychology 1979, vol. 37, No. 11, p. 2049, 2055.

Buam, K., et al., "Perception of Emotions: Measuring decoding accuracy of adult prosodic cues varying intensity", Summer 1998, Journal of Nonverbal Behavior, p. 89-108.

Chen, Qimei, et al., "Attitude toward the Site", Sep. 1999, Journal of Advertising Research, p. 27.

Cohn, J., et al., "A Comparative Study of Alternative FACS Coding Algorithms", tech. report CMU-RI-TR-02-06, Robotics Institute, Carnegie Mellon University, Nov. 2001.

Derbaix, C., "The Impact of Affective Reactions on Attitudes toward the Advertisement and the Brand: A Step toward Ecological Validity", Journal of Marketing Research, vol. 32, No. 4 (Nov. 1995), pp. 470-479.

Ekman, P. & Friesen, W.V., "Manual for the Facial Action Coding System", 1978, 352 pages; Human Interaction Laboratory Department of Psychiatry, University of California.

Ekman, P. & Friesen, W.V., "Unmasking the Face, A Guide to Recognizing Emotions from Facial Clues", 1979.

Ekman, P., "Facial Clues to Deceit", Telling Lies, Clues to Deceit in the Marketplace, Politics, and Marriage, p. 123-161, 1992.

Ekman, P., et al., "Measuring Facial Movement", Environmental Psychology and Nonverbal Behavior, vol. 1, No. 1, p. 56-75, 1976.

Ekman, P., et al., "Facial Signs of Emotional Experience," Journal of Personality and Social Psychology, vol. 39, No. 6, p. 1125-1134, 1980.

Ekman, P., et al., "Final Report to NSF of the Planning Workshop on Facial Expression", Aug. 1, 1992. pp. 1-87, Retrieved from http://mambo.usc.edu/psl/nsf.txt on Jul. 9, 2001.

Essa, I., et al., "Facial Expression Recognition using a Dynamic Model and Motion Energy" M.I.T. Media Laboratory Perceptual Computing Section Technical Report No. 307, Jun. 20-23, 1995, p. 1-8.

Frabotta, David, "Changing Focus", Feb. 21, 2000, Hotel & Motel Management, p. 1, 68.

Gordon-Murnane, Laura "Evaluating Net Evaluators", Feb. 1999, Searcher 7, 2, 57(1).

Hazlett, R., et al. "Emotional Response to Television Commercials: Facial EMG vs. Self-Report", Mar. 1999, Journal of Advertising Research, p. 7-23.

http://dataface.nirc.com/Expression/FACS/body_facs.html, Facial Affect Coding System, Jul. 9, 2001.

Izard, C., et al., "A System for Identifying Affect Expressions by Holistic Judgments (AFFEX)", Instructional Resources Center, University of Delaware, Newark, Delaware (1983).

Izard, C.E., "The Maximally Discriminative Facial Movement Cody System, (Rev. ed.)", Instructional Resources Center, University of Delaware, Newark, Delaware (1983).

Gallup & Robinson, Impact, "CERA—A new System for Measuring Emotion in Advertising", 9:1, Winter 2000, p. 1-2.

Lee, C., et al., "Measuring Influence of the family decision making process using an observational method", 1998 Qualitative Market Research, p. 88-98.

Lien. J., et al., "A Multi-Method Approach for Discriminating Between Similar Facial Expressions, Including Expression Intensity Estimation", Proceedings of the IEEE Conference on Computer Vision and Pattern Recognition (CVPR '98), Jun. 1998.

Lien. J., et al., "Detection, Tracking, and Classification of Action Units in Facial Expression", Journal of Robotics and Autonomous Systems, Jul. 1999, p. 1-39.

(56) References Cited

OTHER PUBLICATIONS

Marcolin, et al., "Assessing User Competence: Conceptualization and Measurement", Information Systems Research. Linthicum: Mar. 2000, vol. 11, Issue 1, p. 37-60.

Sejnowski, T., Computational Neurobiology, http://www.salk.edu/faculty/sejnowski.html, Jul. 9, 2001, Table 11-1 Emotional Predictions, p. 138-139, undated.

Tian, et al., "Recognizing action units for facial expression analysis", IEEE Transactions on Pattern Analysis and Machine Intelligence, vol. 23, No. 2, Feb. 2001, p. 97-115.

"U.S. Appl. No. 13/099,040, Non Final Office Action mailed Apr. 4, 2013", 13 pgs.

* cited by examiner

| Trait | Score | Happiness | Surprise | Skepticism | Dislike | Sadness | Frustration | Anxiety |
|---|---|---|---|---|---|---|---|---|
| Openness | Highest | More | Less | More | More | More | Less | Less |
| Conscientiousness | Highest | Less | Less | More | Less | More | More | More |
| Extraversion | Highest | More | More | More | More | Less | Less | Less |
| Agreeableness | Highest | More | More | More | Less | More | Less | More |
| Neuroticism | Lowest | Less | More | More | Less | Less | More | More |

Figure 2a

Overall Correlation Ratings
*Comparing the Big-Five Traits to four key emotions*

|  | Stability | Extraversion | Openness | Agreeableness | Conscientiousness |
|---|---|---|---|---|---|
| Happiness | 4.63 | 4.01 | 1.84 | 2.88 | 3.38 |
| Sadness | (4.20) | (2.33) | (0.83) | (1.83) | (3.17) |
| Fear | (4.17) |  | (0.33) |  |  |
| Anger | (4.56) | (2.00) | (0.33) | (3.50) | (3.67) |

(5) = High Negative Correlation      High Positive Correlation = 5

0 = No Real Correlation

Figure 2b

| | Norm | Result |
|---|---|---|
| Fear of Loss | 57% | ← |
| Conformity | 43% | ← |
| Resistance to Change | 81% | → |
| Impulsivity | 31% | ← |
| Probability Blinders | 65% | → |
| Self-Deception | 62% | → |
| Fairness Bias | 44% | ← |

Figure 4

Q: At the time of the accident – let's cut right to the chase a little bit more, then. Tell me what happened in the accident. Why don't you just describe it to me first?

A: *Well*, I had a delivery right in front of the place where *the accident happened*. I was pulling in that driveway, trying to make a (wide right turn), and I straddled two lanes – I had my turn signal on. I straddled two lanes of traffic to make that wide right turn because it was *traffic* in and out the driveway, and there's a telephone, there was a (telephone pole) on the curbing.

Key

Neutral
*Strong Negative*
(Weak Negative)
Strong Positive
(Weak Positive)

Figure 12

Q: At the time of the accident – let's cut right to the chase a little bit more, then. Tell me what happened in the accident. Why don't you just describe it to me first?

A: Well, I had a delivery right in front of the place where the accident happened. I was pulling in that driveway, trying to make a wide right turn, and I straddled two lanes – I had my turn signal on. I straddled two lanes of traffic to make that wide right turn because it was traffic in and out the driveway, and there's a telephone, there was a telephone pole on the curbing. *The other party was in the wrong, not me.*

Surprise expression contradicts certainty of statement suggesting made-up this explanation in moment of telling.

*Fear shown, suggesting either person is afraid of consequences – what might compel person to lie – or is in fact misassigning responsibility and guilt.*

Figure 13

METHOD OF ASSESSING PEOPLE'S SELF-PRESENTATION AND ACTIONS TO EVALUATE PERSONALITY TYPE, BEHAVIORAL TENDENCIES, CREDIBILITY, MOTIVATIONS AND OTHER INSIGHTS THROUGH FACIAL MUSCLE ACTIVITY AND EXPRESSIONS

CROSS REFERENCE TO RELATED APPLICATION

The present application claims priority to U.S. Provisional Patent Application No. 61/169,806, filed on Apr. 16, 2009, and entitled "Method of Assessing People's Self Presentation and Actions to Evaluate Personality Type, Behavioral Tendencies, Credibility, Motivations and Other Insights Through Facial Muscle Activity and Expressions", the entire contents of which are hereby incorporated by reference herein in their entirety.

FIELD OF THE INVENTION

The present disclosure relates generally to methods of evaluating people's personality type, behavioral tendencies, credibility, motivations and other such insights. More particularly the present disclosure relates to the use of non-verbal language to gain a better understanding of people's personality type, behavioral tendencies, credibility, motivations and other such insights related to applications including but not limited to personnel hiring, career development, training, internet dating, and the analysis of people involved in law suits as witnesses or in actual or mock/shadow juries.

BACKGROUND OF THE INVENTION

The reality is that people lie to themselves, and to others. Indeed, it's been estimated that the average person lies three times in every ten minutes of conversation. The problem that this lack of inherent honesty poses for those trying to evaluate the skills, nature, knowledge and veracity of another person therefore becomes of fundamental concern to a host of parties, ranging from employers to people evaluating the self-presentation of potential romantic partners or those testifying or otherwise involved in legal matters. Moreover, even when lying is not the issue, understanding the emotional dimension that breakthroughs in brain science have recently documented as crucial to people's decision-making and behavior is difficult, at best, to grasp through verbal input alone. That's because human beings verbal abilities reside in the conscious, rational part of the brain, whereas the older, more subconscious sensory and emotional parts of the brain have "first mover" advantage in people's thought process and therefore often play a dominate role in how people act. Because people don't think their feelings, they feel them, the general need arises to find a solution to the difficulties inherent in relying on the evaluation of words alone to convey meaning and motives in a reliable, insightful manner.

For instance, consider the situation of a company trying to choose which worker to hire for a new job opening. Research indicates that the selection process among job applicants has decidedly checkered results. Even the best measures, like a general mental ability test, a work sample test, and/or integrity tests have been found to be generally no more than 40% to 50% accurate in predicting a choice that proves to work out well once the person gets hired. Considering that turn-over caused by poor personnel selection can cost a company 2 to 7 times an employee's annual salary once lost training costs and other factors are taken into account, clearly companies and all organizations in general would like to improve their odds of choosing suitable personnel.

Moreover, even if the person hired proves to be adequate for the position in functional terms, with a bias toward cognitive ability, the reality is that advances in brain science as well as ever more sophisticated approaches to evaluating, training and promoting personnel for new, often supervisory roles within a company now look to evaluating emotional intelligence (EQ) and potential as well. After all, whether it involves supervising workers or interacting with vendors, business partners, or outside parties like the press, investors and regulators, people skills matter. Therefore, understanding the emotional profile, i.e., the emotional tendencies, and emotionally-fueled attitudes and values of people ranging from in-field supervisors to senior executives, can be of benefit in determining employee's career paths, needs for training, and the like. Unfortunately, at present, instruments like interviews or questionnaires rely on assessing the emotional profile and other qualities of an individual through rationally oriented, cognitively filtered means that emphasize formulating thoughts in written or oral form.

Another sample instance where relying on written or oral input alone to evaluate another person's personality type, behavioral tendencies, credibility, motivations and other such insights can prove to be problematic is in trying to assess potential romantic partners. Traditionally, people meeting one another did so in person or through mutual contacts like family members or friends. But in recent years, changes in society ranging from the frequency of moves to new locations, the anonymity of modern life, and the emergence of the internet have combined to make internet dating services, matchmaker dating services, and the like, a prevalent set of options for people looking to enrich their personal life through meeting others that they might date, marry or cultivate as special friends. At present, most of these dating services that have arisen hope to match people based on their submission of answers to build a profile that purports to identify their interests, habits, personality type, emotional make-up, and so forth. Whether that input is reliable, however, remains a serious issue as clearly people can be readily inspired to enhance their strengths and mitigate blemishes that might stand in the way of their securing an unsuspecting partner.

Yet another sample instance where the current reliance on verbal or written self-presentation alone poses a problem involves trying to assess people's self-presentation in courtroom settings. At present, lawyers and their clients rely first and foremost on the oral and written statements of witnesses, defendants, prospective jury members, and members of a mock or shadow jury that a law firm may use to test its lines of argumentation in order to assess the relevancy, credibility of people's testimony or view points. At times, lawyers may certainly seek to supplement those oral or written statements with attempts to read the "body language" of people. But given research that indicates that even the best detectors of lying—secret service agents, followed by psychologists—are at no better than chance levels of detecting deception, certainly a means of evaluating the veracity of people's statements, knowledge, biases, etc., would be hugely beneficial in guarding against errors in strategies formulated based on the slippery medium of language alone.

While the above instances by no means exhaust the range of issues the various embodiments of the present disclosure can be applied against, they do represent instructive instances where the study of facial muscle activity and expressions could address an outstanding problem. At the same time, opportunities such as being able to evaluate the emotional content of human-interest video posted to the internet to evaluate its content more adroitly, or of being able to evaluate the emotional content of video of people shopping in a store in order to provide better customer service for them are among other possibilities.

Standardized methods already exist to assess an individual's personality. For example, at present, job applicants whose personality is being assessed are most likely to be given a written exam that reflects either the Myers-Brigg 4-factor model of personality type or else the now more critically acclaimed Big Five Factor model of personality type, sometimes known as McCrae and Costa, in honor of two of its most notable psychologist developers. The Big Five Factor model is described in Mathews, G., Deary, I., and Whiteman, M., *Personality Traits*, Cambridge University Press, Cambridge, U.K., (2003), Wiggins, J., editor, The Five-Factor Model of Personality, Guilford Press, New York City (1996), McCrae, R., Costa, P., *Personality in Adulthood: A Five-Factor Theory Perspective*, Guilford Press, New York City (2003), and specifically in relation to evaluating personnel, in Howard, P. and Howard, J., *The Owner's Manual for Personality at Work*, Bard Press, Austin, Tex. (2001), each of which is hereby incorporated by reference in its entirety herein. However, despite Howard's work in evaluating personnel, the reality is that the Big Five Model for personality types can also be applied to assessing a potential romantic partner among a range of other applicants, casting for movies, to determine a child's personality type to ensure a compatible tutor or best practices for educational purposes, which player to draft to join a team sport like the NBA or NFL, etc. The Big Five Factor model is sometimes referred to by the acronym of OCEAN because it rests on the conclusion that the traits of openness, conscientiousness, extraversion, agreeableness and neuroticism (or emotional stability) form the basis of people's personalities.

Additionally, a new field that blends psychology, neurobiology and economics called Behavioral Economics has recently emerged that could prove useful. This field is premised on the belief, aided by breakthroughs in brain science, that people are predominantly emotional decision-makers. Eliciting answers to questions based on the key principles of Behavioral Economics, such as loss aversion, conformity, fairness bias, etc., provides the additional benefit of zeroing in on the emotional dimension of how personnel performs on the job, or how much a person in general is susceptible to the biases that this new field of economics zeroes in on, an area that the traditional, rational, cognitively filtered approaches to assessing personnel have generally either ignored or been unable to capture other than through written and verbal, cognitively filtered means. Prominent works in the field of Behavioral Economics include Wilkinson, N., *An Introduction to Behavioral Economics, Palgrave*, London, U.K. (2008), Ariely, D., *Predictably Irrational: The Hidden Forces That Shape Our Decisions*, HarperCollins, New York City (2008), and Thaler, R., Sunstein, C., *Nudge: Improving Decisions about Health, Wealth, and Happiness*, Yale University Press, New Haven, Conn. (2008), each of which is hereby incorporated by reference in its entirety herein.

Whether in regard to Myers-Briggs, The Big Five Factor model, Behavioral Economics or some other such model for assessing personality type, the array of testing methods in practice all generally rely on tests with written self-assessment scoring, buttressed at times by additional assessments from individuals with presumably good, intimate knowledge of the person subject to testing, or third parties. Because of the susceptibility of self-reporting to willful or unconscious deception, a more reliable method is sought for capturing an understanding of how the person fits that particular model. To date, the few attempts to use psycho-physiological methods to gauge personality type and link it to the Big Five Model, for example, have involved other techniques like electroencephalography (EEG), heart rate, sweat gland activity or functional brain imaging. These approaches suffer from requiring the use of electrodes or other invasive monitors and also have not attempted more than typically one or two of the five trait dimensions that make up the Big Five Model, exploring traits like extraversion or at times neuroticism, without attempting to be comprehensive in finding psycho-physiological correlates for all of the five traits.

Thus, there exists a need in the art for a better way to assess non-verbal language to gain a better understanding of people's personality type, behavioral tendencies, credibility, motivations and other such insights.

BRIEF SUMMARY OF THE INVENTION

The present disclosure, in one embodiment, relates to a method of assessing an individual through facial muscle activity and expressions. The method includes receiving a visual recording stored on a computer-readable medium of an individual's non-verbal responses to a stimulus, the non-verbal response comprising facial expressions of the individual, so as to generate a chronological sequence of recorded verbal responses and corresponding facial images. The computer-readable medium is accessed to automatically detect and record expressional repositioning of each of a plurality of selected facial features by conducting a computerized comparison of the facial position of each selected facial feature through sequential facial images. The contemporaneously detected and recorded expressional repositionings are automatically coded to an action unit, a combination of action units, and/or at least one emotion. The action unit, combination of action units, and/or at least one emotion are analyzed to assess one or more characteristics of the individual to develop a profile of the individual's personality in relation to the objective for which the individual is being assessed.

The present disclosure, in another embodiment, relates to a method of assessing an individual through facial muscle activity and expressions. The method includes receiving a visual recording stored on a computer-readable medium of an individual's response to a stimulus, a first portion of the individual's response comprising facial expressions of the individual, so as to generate a chronological sequence of recorded facial images. The computer-readable medium is accessed to automatically detect and record expressional repositioning of each of a plurality of selected facial features by conducting a computerized comparison of the facial position of each selected facial feature through sequential facial images. The contemporaneously detected and recorded expressional repositionings are automatically coded to an action unit, a combination of action units, and/or at least one emotion. The action unit, combination of action units, and/or at least one emotion are analyzed against a second portion of the individual's response to the stimulus to assess one or more characteristics of the individual.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the embodiments will be better understood from the following description taken in conjunction with the accompanying Figures, in which:

FIG. 2A is a chart showing a correlation of traits to emotions according to one embodiment of the present disclosure.

FIG. 2B is a chart showing self-reported emotions and their relation to the Big Five Factor traits according to one embodiment of the present disclosure.

FIG. 4 is a chart showing Behavioral Economics tendencies according to one embodiment of the present disclosure.

FIG. 12 is an analyzed facial coding transcript according to one embodiment of the present disclosure.

FIG. 13 is an analyzed transcript indicating an emotional display in real time according to one embodiment of the present disclosure.

DETAILED DESCRIPTION

Figure 1:
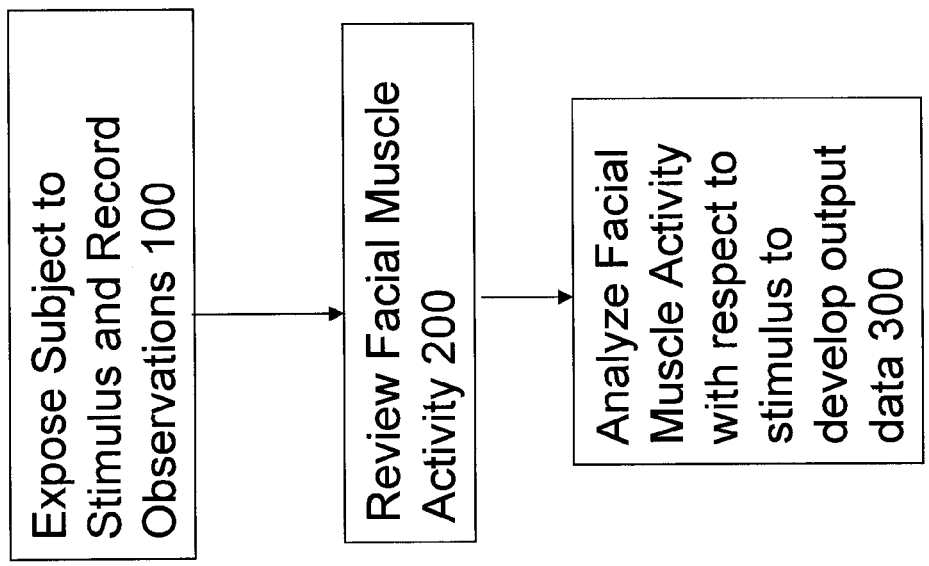
FIG. 1 is a flow chart of showing a method according to one embodiment of the present disclosure.

As utilized herein, the phrase "action unit" or "AU" can include contraction or other activity of a facial muscle or muscles that causes an observable movement of some portion of the face.

As utilized herein, the phrase "appeal" can include the valence or degree of positive versus negative emoting that a person or group of people show, thereby revealing their degree of positive emotional response, likeability or preference for what they are saying/hearing/seeing. The appeal score can be based on which specific action units or other forms of scoring emotional responses from facial expressions are involved.

As utilized herein, the term "coding to action units" can include correlating a detected single expressional repositioning or combination of contemporaneous expressional repositionings with a known single expressional repositioning or combination of contemporaneous expressional repositionings previously recognized as denoting a specific action unit whereby the detected single expressional repositioning or combination of contemporaneous expressional repositionings can be categorized as indicating the occurrence of that type of action unit. Types of action units utilized in the method of this invention may include for example, but are not limited to, those established by the Facial Action Coding System ("FACS").

As utilized herein, the term "coding to emotions or weighted emotional values" can include correlating a detected single expressional repositioning or combination of contemporaneous expressional repositionings with a known single expressional repositioning or combination of contemporaneous expressional repositionings previously recognized as denoting one or more specific emotions whereby the detected single expressional repositioning or combination of contemporaneous expressional repositionings can be categorized as indicating the occurrence of those types of emotions. The emotion(s) coded from each detected single expressional repositioning or combination of contemporaneous expressional repositionings can optionally be weighted as an indication of the likely strength of the emotion and/or the possibility that the expressional repositioning was a "false" indicator of that emotion.

As utilized herein, the phrase "emotion" can include any single expressional repositioning or contemporaneous combination of expressional repositionings correlated to a coded unit. The expressional repositionings can be coded to action units and then translated to the various emotions, or directly coded to the various emotions, which may include but are not necessarily limited to anger, disgust, fear, happiness (true and social smile), sadness, contempt and surprise as set forth in the Facial Action Coding System ("FACS"), and the additional emotional state of skepticism.

As utilized herein, the phrase "engagement" can include the amount or volume and/or intensity of emoting, perhaps by action unit activity, that a person or group of people show in response to a given stimulus or line of inquiry or presentation, or in the case of a group of people, the percentage of people with a code-able emotional response to a stimulus, topic, line of inquiry or presentation.

As utilized herein, the phrase "expressional repositioning" can include moving a facial feature on the surface of the face from a relaxed or rest position, or otherwise first position, to a different position using a facial muscle.

As utilized herein, the phrase "facial position" can include locations on the surface of the face relative to positionally stable facial features such as the bridge of the nose, the cheekbones, the crest of the helix on each ear, etc.

As utilized herein, the term "impact" can include the potency or arousal or degree of enthusiasm a person or group of people show based on the nature of their emoting, based on for example, specific action units, their weighted value, and/or the duration of the action units involved when that is deemed relevant and included in the weighting formula.

As utilized herein, the term "interview" can include asking at least one question to elicit a response from another individual regarding any subject. For example, this can include asking at least one question relating to assessing the person's characteristic response to business situations in general, to situations likely to relate to specific traits among the Big Five Factor model, to questions that pertain to Behavioral Economic principles, or to creating scenarios in which the person is meant to become an actor or participant for the purpose of observing that person's behavior until the simulated situation. An interview may be conducted in any number of settings, including, but not limited to seated face-to-face, seated before a computer on which questions are being posed, while enacting a scenario, etc.

As utilized herein, the term "Behavioral Economics" can include the school of economics that maintains that people engage in behavior that might not be for the classic economic principle of achieving greatest utility but may, instead, reflect the influence of irrational emotions on their behavior.

As utilized herein, the term "Behavioral Economics principles" can include some or all, and not limited to the seven principles of fear of loss, self-herding (conformity), resistance to change, impulsivity, probability blinders (faulty evaluation based on framing, mental accounting, priming, etc.), self-deception (ego), and fairness bias.

As utilized herein, the term "Big Five Factor model" or OCEAN can include some or all, and is not limited to the five personality traits of openness, conscientiousness, extraversion, agreeableness and neuroticism (or stated more positively, emotional stability) that form the basis of the personality model that rests on those five traits as developed by academics such as McCrea and Costa.

As utilized herein, the term "scenario" shall include a case where the interview might involve not just questions to be answered but also a situation or scenario. For example, a scenario may include asking a potential sales force hire to simulate the sequence of making a cold phone call to a prospect and detecting what emotions appear on the person's face in being given the assignment, as well as in enacting it or discussing it afterwards.

Among its embodiments, the present disclosure can be directed to overcoming the problems inherent in relying on verbal input alone in assessing the personality type, behavioral tendencies, credibility, motivations, etc., of people by supplementing or replacing such verbal analysis with the analysis of people's facial muscle activity and expressions.

A method of doing so, applicable across instances or opportunities such as those detailed above in the Background, is illustrated in FIG. 1 and may involve first either watching in real-time or capturing on video the non-verbal expressions and reactions of people to emotional stimulus 100. Said stimulus can be anything ranging from a structured interview with questions, to their behavior during planned or impromptu scenarios (such as a sales person enacting a cold call to simulate ability to make such calls), to behavior and responses captured intentionally or inadvertently on video, to verbal and non-verbal expressions during a trial or a deposition, etc.

Step one of the method as described above, in one embodiment, for instance, may use questions asked or the scenarios used that are standardized to allow for norms and a standard by which to therefore measure the degree to which the emotional response detected is suitable for the job position in question. For example, the same five questions, each related to a different way of assessing a person's work tendencies or capabilities, or to determine a specific number, set of instructions for, and amount of time allotted for a scenario to be enacted could be used.

Figure 3:
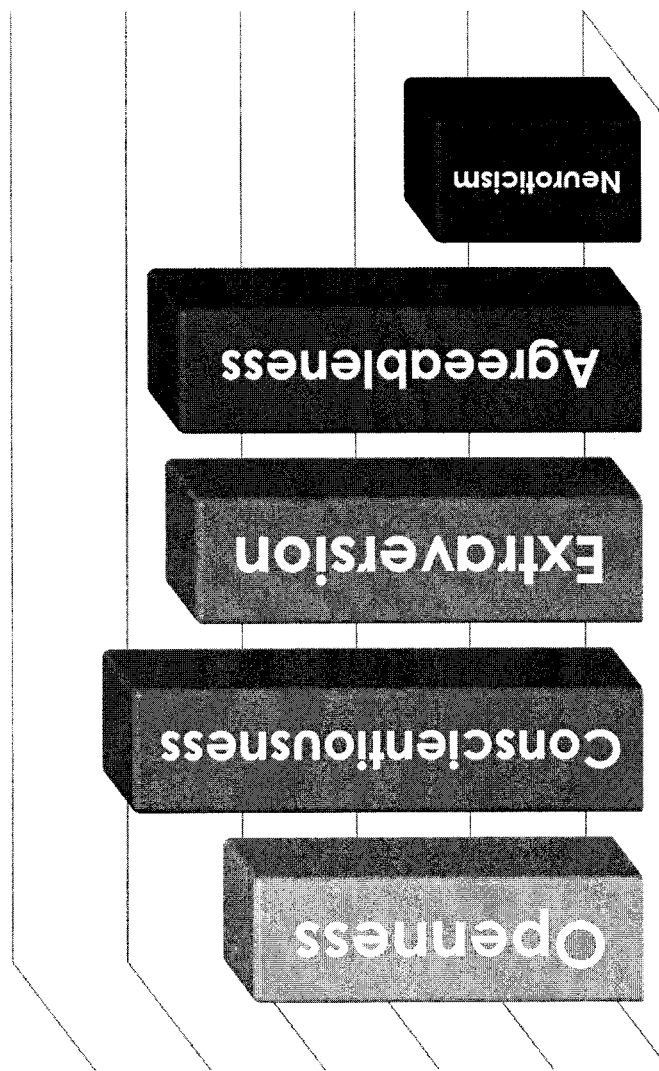
FIG. 3 is a diagram showing the Big Five Factor model sample results according to one embodiment of the present disclosure.

One embodiment may use standardized questions to determine a person's Big Five Factor model personality type through a structured interview that can include, for example but not limited to, one or more questions per each of the OCEAN traits, for the purpose of capturing emotional data that can then be correlated to personality type. This goal could be achieved on a standard basis by profiling the mixture and predominant display of emotions that best fits a given Big Five Factor personality trait. FIGS. 2a and 2b are charts that generally show manners in which some emotions may be linked to each of the OCEAN traits. FIG. 3 is an example graphic representation of a person's Big Five Model personality type as revealed based on the facial muscle activity or expressions results from a sample piece of video and/or specific line of questions.

Another embodiment may use scenarios and/or questions to evaluate a person in regard to their behavioral economics. The questions could elicit answers to the key principles such as loss aversion, conformity, fairness bias, etc. One or two, or another suitable number of questions, for example, can be asked specific to aspects of the key tenets of Behavioral Economics, such as the set shown in FIG. 4. FIG. 4 is an example, graphic representation of how the facial muscle activity or expressions results, in alignment with biases that pertain to Behavioral Economics, reveal the tendencies of the person or group of people to be susceptible to those behavioral vulnerabilities. A norm might, for instance, reflect the degree to which people are emotionally susceptible to a given tendency, based on a formula of specific emotions they display most prominently in response to a given question, with the result showing whether they are above, below, or within a specified range of what people reveal emotionally in regards to that tendency.

Figure 5:
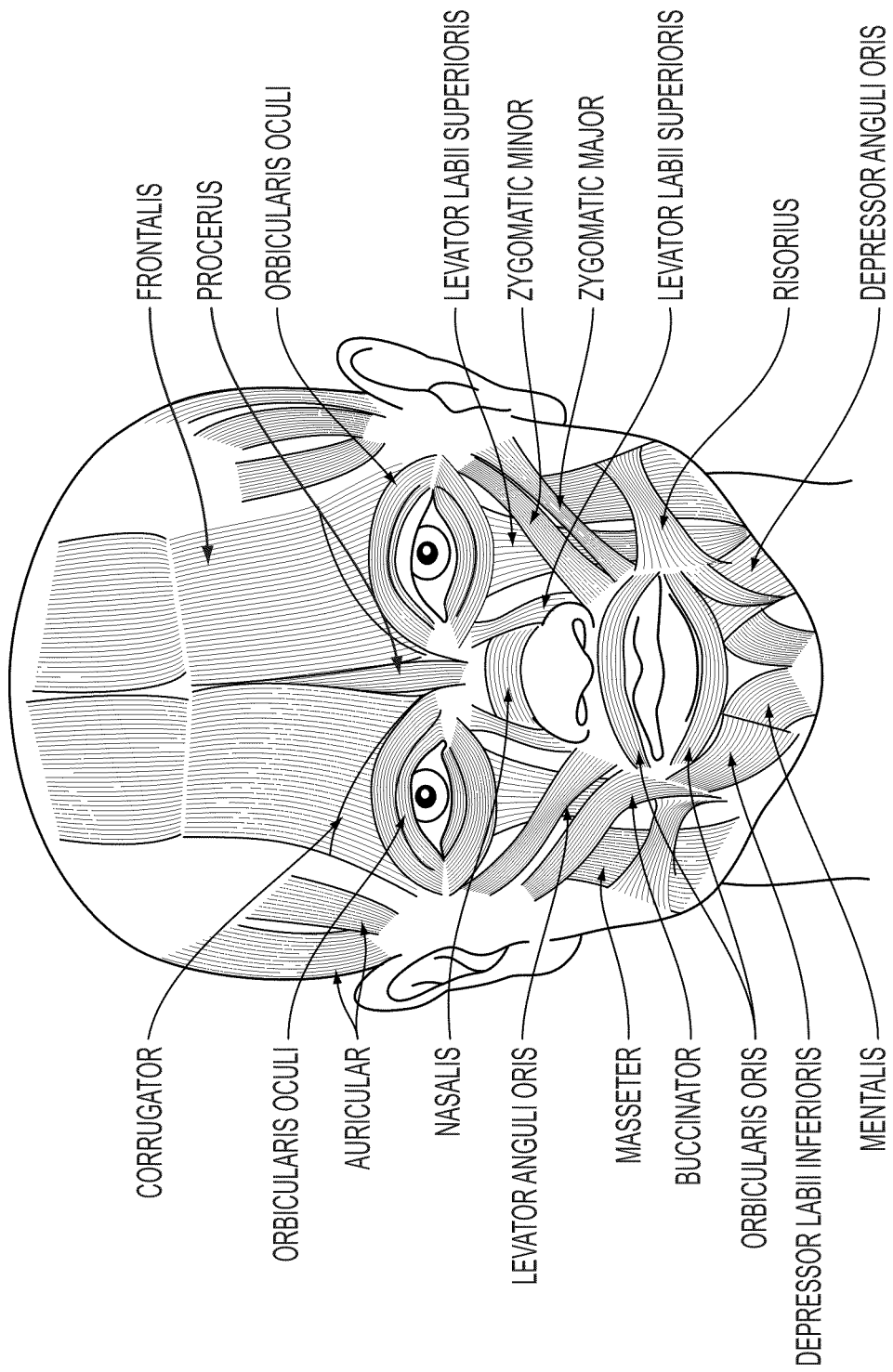
FIG. 5 is an illustration of various facial muscles useful to detect emotions according to one embodiment of the present disclosure.

Referring back to FIG. 1, a second step 200 may involve observing in real-time the facial muscle activity and expressions of the people in question or of reviewing the video files of same. There are some 43 facial muscles that might be taken into account for the purpose of detecting singular instances of muscle movements and expressions, or of posed or held expressions, or patterns of muscle activity movements over time. FIG. 5 is a illustration of a human face indicating the location of several facial features which can be conveniently utilized. This observation or review can involve, for example, noting the general mood or emotional state of an individual, such as sad, happy, angry, etc., by means of general patterns of movement or state of expression, or by specific movements as they relate to given emotions.

Step two of the method can utilize standards to analyze emotions. In this case, among the approaches available for analyzing facial muscle activity and expressions, one option generally stands out among the others for its rigor and extensive documentation. That option is known as facial coding. Facial coding originated with Charles Darwin, who was the first scientist to recognize that the face is the preferred method for diagnosing the emotions of others and of ourselves because facial expressions are universal (so hard-wired into the brain that even a person born blind emotes in a similar fashion to everyone else), spontaneous (because the face is the only place in the body where the muscles attach right to the skin) and abundant (because human beings have more facial muscles than any other species on the planet). Facial coding as a means of gauging people's emotions through either comprehensive or selective facial measurements is described, for example, in Ekman, P., Friesen, W. V., *Facial Action Coding System: A Technique for the Measurement of Facial Movement* (also known by its acronym of FACS), Consulting Psychologists Press, Palo Alto, Calif. (1978), which is hereby incorporated by reference in its entirety herein. Another measurement system for facial expressions includes Izard, C. E., *The Maximally Discriminative Facial Movement Coding System*, Instructional Resources Center, University of Delaware, Newark, Del. (1983), which is also hereby incorporated by reference in its entirety herein.

In accordance with FACS, the observation and analysis of a person's facial muscle activity or expressions can therefore be conducted by noting which specific muscle activity is occurring in relation to the FACS facial coding set of muscle activities that correspond to any one or more of seven core emotions: happiness, surprise, fear, anger, sadness, disgust and contempt or others such as might be determined in the future. According to FACS, there are approximately 20 or so facial muscle activities that on their own or in combination with other muscle activities—known as action units or AUs—can be correlated to the seven core emotions. To engage in facial coding properly, an observer would want to be systematic by reviewing a given person's video files to establish, first, a baseline of what expressions are so typical for the person as to constitute a norm against which changes in expression might be considered. Then the video files would be watched in greater depth, with slow-motion, freeze-frame and replays necessary to document which specific AUs happen and at what time interval (down to even $\frac{1}{30}^{th}$ of a second) to enable review or cross-checking by a second facial coder in the case of manual coding, or human checkers to verify in the case of semi- or fully-automated facial coding. See by way of reference, Table Two and Table Three in U.S. Pat. No. 7,113, 916 (granted Sep. 26, 2006 to inventor), which is hereby incorporated by reference in its entirety herein.

Another option for analyzing emotions is disclosed in *Proceedings of Measuring Behavior* 2005, Wageningen, 30 Aug.-2 Sep. 2005, Eds. L. P. J. J. Noldus, F. Grieco, L. W. S. Loijens and P. H. Zimmerman and is incorporated by reference herein in its entirety. The article details a system called FaceReader™ from VicarVision that uses a set of images to derive an artificial face model to compare with the expressions it is analyzing. A neural network is then trained to recognize the expressions shown through comparison between the expression and the model.

Referring back to FIG. 1, a third step 300 can be to, in some fashion, assemble one's data of what was seen in terms of facial muscle activity and expressions in order to draw some conclusions. Such analysis can range, for example, from noting the person's general mood or characteristic emotion or emotional displays, to correlating their emotional reaction to a specific question, situation, environment (e.g., in the case of a shopper) or stimulus (e.g., in the case of a mock jury member, for instance, responding to a visual aid being considered for display in court to make a point). In addition, potential discrepancies or notable instances where a person's self-representation of facts, or attitudes, etc., seem at odds with the emotions evident might be worthy of noting for further exploration. Such analysis could also conclude that the person is in general or in regards to specific questions or stimuli of a positive, neutral (non-expressive or ambivalent) or negative emotional disposition, for example.

Figure 6:
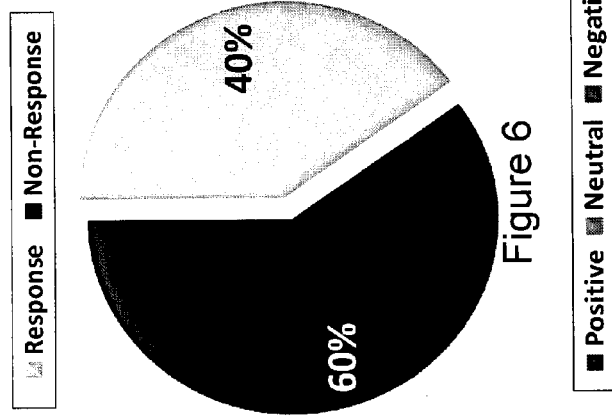
FIG. 6 is a diagram showing Engagement levels according to one embodiment of the present disclosure.

Step three of the method can be implemented by deriving a standard set of measures to be taken from the facial coding results. As an outgrowth of what was just described above, this approach can benefit from noting which AUs occur in relation to what specifically is being said, by question, by subtopic within the answer given, or in relation to a stimulus shown, etc. Then the action units or AUs can be tallied such as to arrive at an array of statistical outputs. One that may be of interest in a range of situations including, for example, whether a job applicant is enthusiastic about a given portion of the job role, whether a potential romantic partner really enjoys an activity you like, or if a potential witness or jury member is riled up by an aspect of the case in question, is to track engagement or emotional involvement level. This measure can be taken, for instance, by considering the amount of time (e.g., duration) when a person was expressing an emotion while talking on a given topic, the amount of AUs the person showed (e.g., volume), or in a mock jury presentation, for instance, the percentage of people who expressed an emotion when a line of argumentation was tried out. FIG. 6 is an example, graphic representation to indicate the amount of emoting, by action unit, based on duration or volume to indicate how motivated or engaged a person or people are by what they are saying/hearing/seeing/doing. When a plurality of subjects are involved, such as with a mock jury, then a percentage of the subjects who are emoting during the presentation of a particular topic or line or argumentation can also be used.

Figure 7:
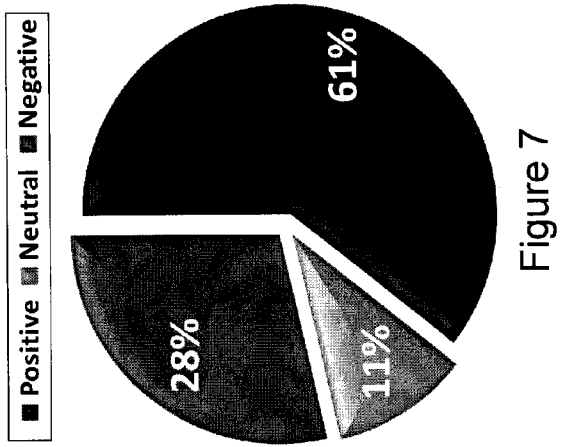
FIG. 7 is a diagram showing overall emotion by type according to one embodiment of the present disclosure.

In terms of statistical output, another way that the facial coding results can be depicted is to provide a percentage of positive, neutral or negative response to a given question, scenario, etc. For instance, one systematic approach could be to consider a person as having had a predominantly positive reaction to a posed question, answered by said person, if that person, whether a job applicant or potential romantic partner or potential jury member, for instance, emoted showing happiness and/or surprise at least 50% of the time during the response. In such a case, a neutral response might be based on emoting happiness and/or surprise for 40 to 50% of the emoting during the response, whereas a response categorized as negative for facial coding purposes would then fall below the 40% mark. By way of example, FIG. 7 is a sample graphic representation of the percentage by which a person or group of people might be predominantly positive, neutral or negative regarding what they might be saying/hearing/seeing/doing during a specific point in an interview, for instance, or over the duration of an interview, mock jury presentation, etc.

Figure 8:
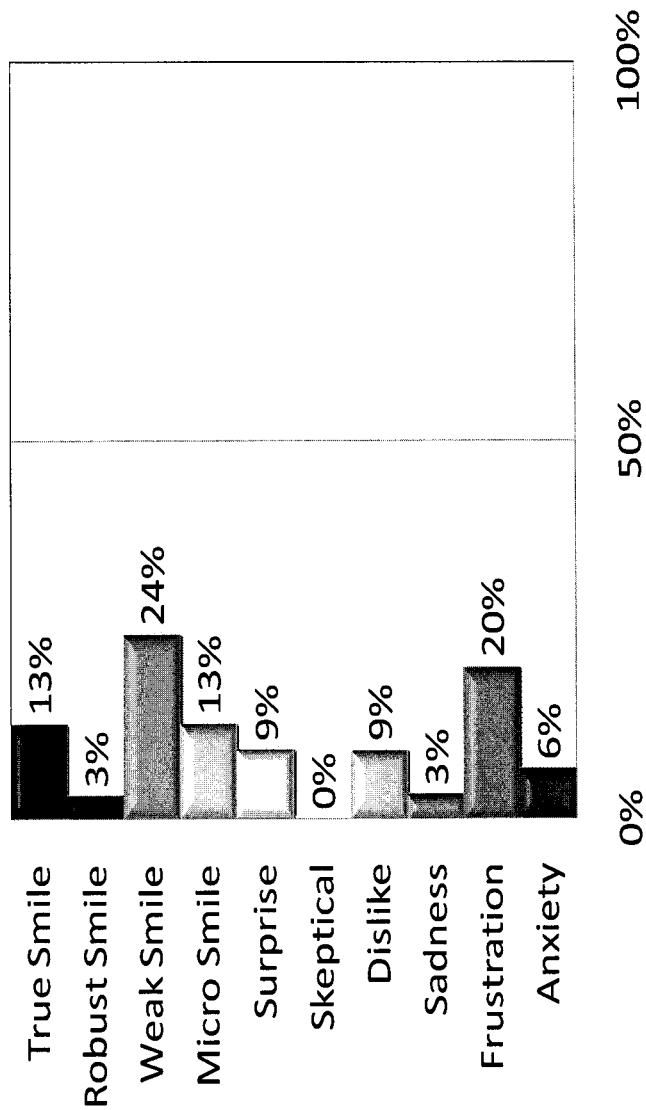
FIG. 8 is a chart showing an emotional profile according to one embodiment of the present disclosure.

In terms of statistical output, yet another output that can be used is to document the degree to which the emotions shown can be divided up into either the seven core emotions or some other type of systematic display of results. One embodiment can be to take the FACS seven core emotions and divide them into, for example, ten emotional states, five positive and five negative. We could then use AUs (identified by number: see FACS) to represent the specific emotions. For example, the positive emotional states could comprise a true smile (AU 6+12) or the highest true of happiness, a robust social smile (AU 12) with cheeks prominently raised, a weak social smile (AU 12) with checks barely raised and teeth not showing or barely, a micro-smile (AU 12) when the smile is unilateral and perhaps also brief, and surprise (AU 1, 2, 5 and 26 or 27 or potentially any combination thereof) as the final element of a positive reaction, or else with surprise treated as a neutral expression, or as positive or negative depending on what other type of emotion is expressed simultaneously or immediately thereafter. Meanwhile, in regard to the negative emotional states, there could be dislike (a combination of disgust and contempt, involving potentially AUs 9, 10, 14, 15, 16, 17, 25 or 26 or a combination thereof or singularly), sadness (AU 1, 4, 11, 15, 25 or 26 and possibly 54 or 64 or a combination thereof or singularly), frustration (AU 4, 5, 7, 10, 17, 22, 23, 24, 25, 26 or a combination thereof or singularly), or anxiety, namely fear (AU 1, 2, 4, 5, 20, 25, 26, 27 or a combination thereof or singularly). That leaves skeptical, which in one embodiment might constitute a smile to soften the "blow" as a negative or sarcastic comment is being made. FIG. 8 is an example, graphic representation of the specific emotions that a person or people are revealing in response to what they are saying/hearing/seeing/doing regarding a specific topic or scenario being enacted or line of argumentation, as described above.

Another embodiment of the scoring system for AUs relative to specific emotions might be to take into account the various combinations of AUs that can constitute a given emotion along a couple of lines of development. One way can be to treat each AU individually and assign its occurrence by even percentages to each and every pertinent emotion to which it might apply. A second embodiment here might be to, in contrast, weight each AU by ever greater degrees in favor of a given emotion when other AUs are simultaneously or in close timing also evident, whereby the variety of AUs being shown in a short time span can, for instance, tilt the result in favor of concluding that a given emotion is the predominant emotion being displayed. By way of example, consider a case where AU 2 is shown by itself. As this corresponds in FACS terms to both fear and surprise, by itself it might be assigned on a 50% fear and 50% surprise basis. But if AU 2 occurs in proximity to AU 11, which fits sadness only, then AU 11 might be 100% assigned to the sadness category, with AU 2 in turn now receiving a 66% weighting in favor of sadness and now only 33% surprise. Other such systematic formulas could follow to allow for the many combinations of AUs possible. For example, see U.S. patent application Ser. No. 11/062,424 filed Feb. 20, 2005 and incorporated herein by reference in its entirety. See also U.S. Pat. Nos. 7,246,081 and 7,113,916 issued to the Applicant and also incorporated herein by reference in their entirety.

Figure 9:
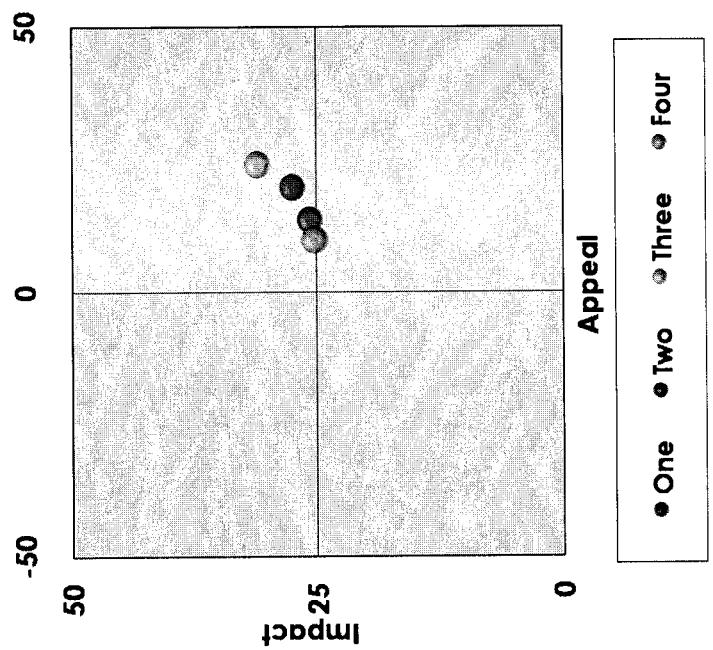
FIG. 9 is a diagram showing an impact and appeal chart according to one embodiment of the present disclosure.

In terms of statistical output, yet another output that can be used is to graph the results onto a quadrant chart. In this case, the two vectors that might be used could be drawn from psychology, which often considers the potency or arousal dimension of, say, an emotional response, herein referred to as impact, along with the valence or degree of positive versus negative emotional response, or likeability or preference, herein referred to as appeal, as a possible second dimension or vector in presenting the results on a quadrant chart. FIG. 9 is an example, graphic representation of the impact and appeal values, shown on a quadrant chart, to indicate by person, in a lineup of positive job hires, for instances, who emotes with the most impact and/or appeal to a particular question versus another, or on average for one person versus others.

In another embodiment, each of the AUs singularly or perhaps by virtue of an array of combinations can in each instance be assigned an impact or appeal weight developed in a formula. In turn, each impact and appeal value for each type of emoting that occurs in response to a given question, during a scenario, or overall in response to, for instance, a mock jury presentation or emotional profile of a potential romantic partner could then be accumulated to arrive at the type of presentation of results shown in FIG. 9. Alternatively, the impact and appeal scores could have its accumulative total divided by time duration, by number of people involved, be shown against a norm, and so forth. This is also done in U.S. patent application Ser. No. 11/062,424 further describes the use of weighted values and weighted formulas.

Figure 10:
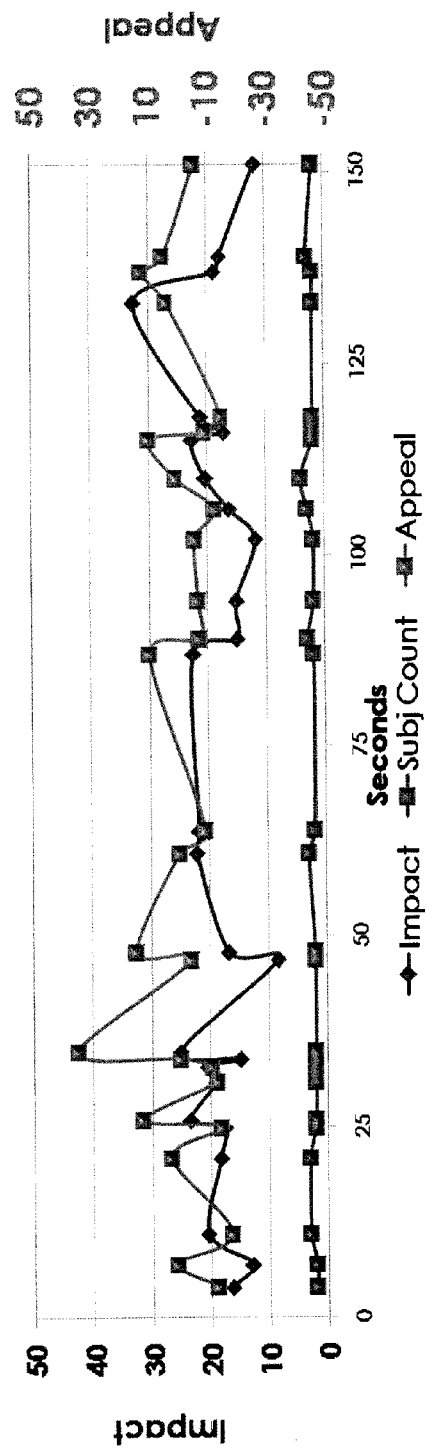
FIG. 10 is a chart showing a second-by-second impact and appeal according to one embodiment of the present disclosure.

In terms of statistical output, yet another output that can be used while bearing a potential relation to the impact and appeal scoring approach is to construct a timeline. In this case, for example, a data point or feeling point can be shown when at least two subjects out of a sample of subjects had a code-able emotional response within the same split-second to a stimulus. Such an approach can still work well with a mock jury, for instance. In another embodiment, however, where individuals are involved, an emotional data point might be shown each and every time emoting takes place and the subject count would, if included, note the amount of AUs that were occurring at that time, or else perhaps their level of intensity, seeing as FACS now has 5 levels of intensity for each AU shown. FIG. 10 is an example, graphic representation of the impact and appeal values, based on proprietary scoring weights for the action units shown by a person or group of people, to a statement, audio presentation, etc., to indicate at which points in the presentation people are emoting most and in what ways to reveal the relevancy and interest and type of response they have to the presentation being given.

Figure 11:
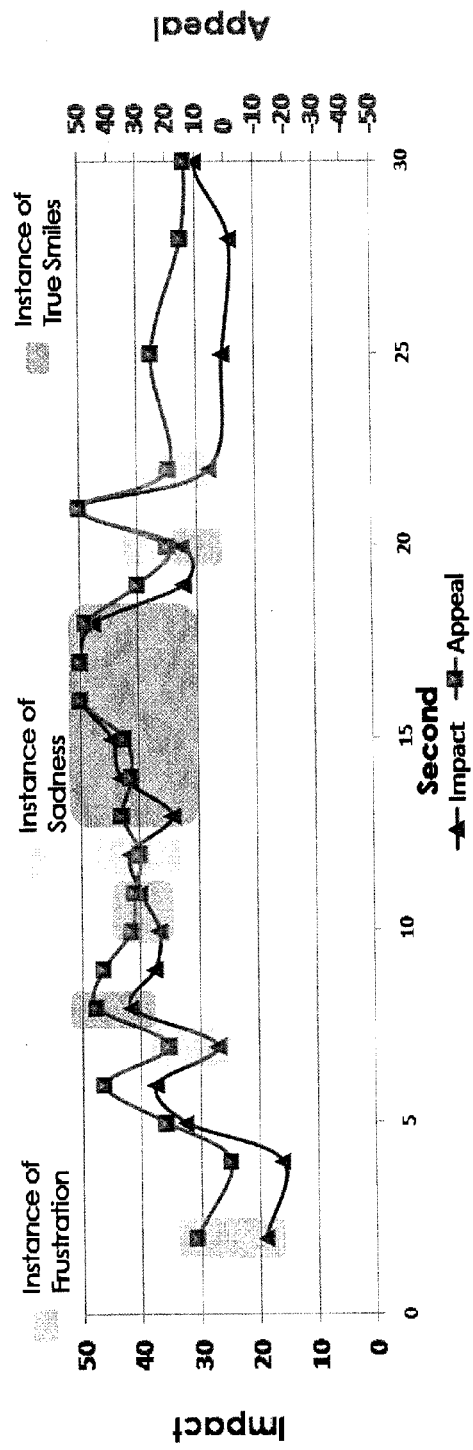
FIG. 11 is a chart showing an emotional display in real time according to one embodiment of the present disclosure.

In terms of statistical output, yet another output that can be used is to augment the second-by-second chart shown in FIG. 10 by highlighting which emotion or emotions exist in relation to each emotional data point or else are perhaps predominant at certain points when response level is greatest. An example of this type of output option is shown in FIG. 11.

In terms of statistical output, yet another output that can be used is to take a given transcript, whether from a witness with a videotaped deposition, a person eligible for jury selection, a person in a job interview, or a person who might be a potential romantic partner, etc., and correlate the transcribed transcript such that when the person emoted, that response can be shown in relation to what was being said or heard at that given point in time. This correlation can in turn be shown in a variety of ways, including but not limited to, whether the emotions shown are positive, neutral or negative based on the predominant emotion(s) shown, or by percentage based on a formula, and/or by considering the type of AU involved and thus the degree to which the emotional response is positive or negative in terms of valence. FIG. 12 is an example, graphic representation of when a transcript of somebody's response to a question, statement, or videotaped deposition, for instance, has been coded to reveal the positive or negative valence or appeal of that person at that point in the transcript. Alternatively or in addition, the specific emotions a person is showing in response to what they are saying/hearing/seeing could also be incorporated.

In terms of statistical output, yet another output that can be used is to construct a variation of the FIG. 12 example, wherein the coded transcript can likewise be flagged to indicate discrepancies between the coded transcript and the topic in question, in cases where a person's veracity might be suspect or heavy in emotive volume and, therefore, worthy of further investigation. An example of this type of output is shown in FIG. 13.

Figure 14:
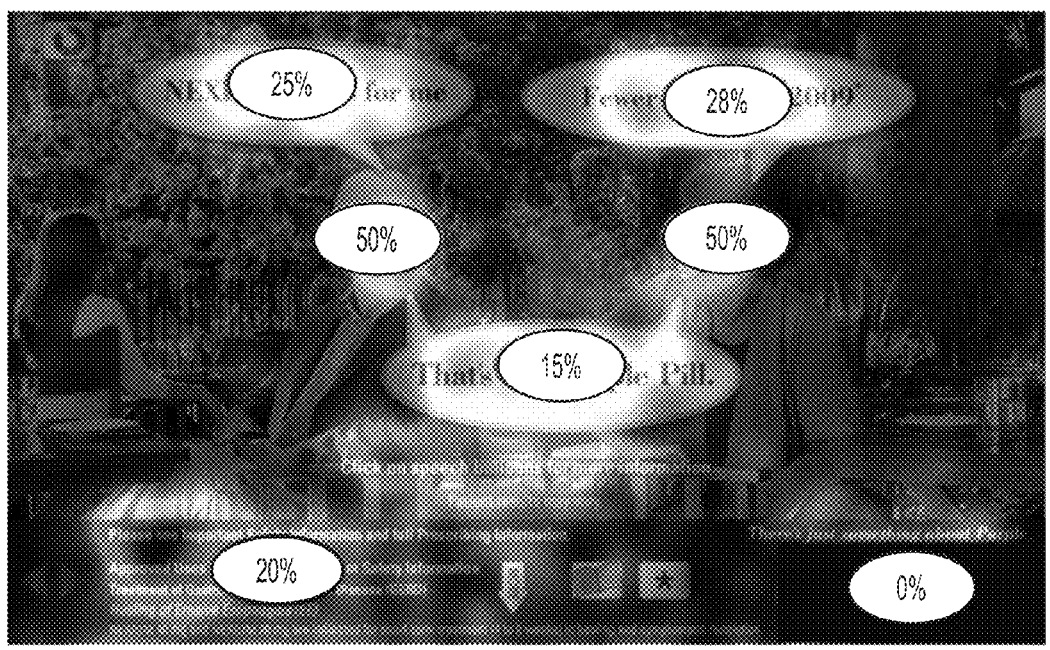
FIG. 14 is a picture showing eye tracking linked with facial coding according to one embodiment of the present disclosure.

In terms of statistical output, yet another output that can be used is to consider an example like a mock jury being shown a visual aid intended for courtroom display and discern where the subjects look based on the use of eye tracking and how they feel about what they are taking in, using facial coding. For background, see U.S. pending patent application Ser. No. 11/491,535, titled "Method and Report Assessing Consumer Reaction to a Stimulus by Matching Eye Position with Facial Coding", filed by this inventor on Jul. 21, 2006, under, the entirety of which is hereby incorporated by reference herein. Such synchronization of eye tracking results and facial coding results can of course be utilized in other fashions, too, for matters involving personnel such as how a job applicant inspects and reacts to company advertising, ethics guidelines, etc. FIG. 14 is an example, graphic representation of how people have emoted in response to particular details of, for instance, a presentation of a visual aid that might be used in court whereby the stimulus in question has also been subject to eye tracking analysis, with the facial coding results and the eye tracking results synchronized. The percentages shown here indicate the degree of positive emotional response that specific areas of the stimulus created in the observer(s), with the hot-spot heat map shown here indicating by shades of white to different levels of grey to black the decreasing degrees to which the observer(s) focused on that detail of the stimulus such that their eye movements were arrested, or stayed with a given detail, as recorded as eye fixations lasting at least $\frac{1}{50}^{th}$ of a second. Alternatively, a "bee-swarm" output of results could show by observer(s) where each given person's eye gaze went to in absorbing the details of a stimulus.

Figure 15:
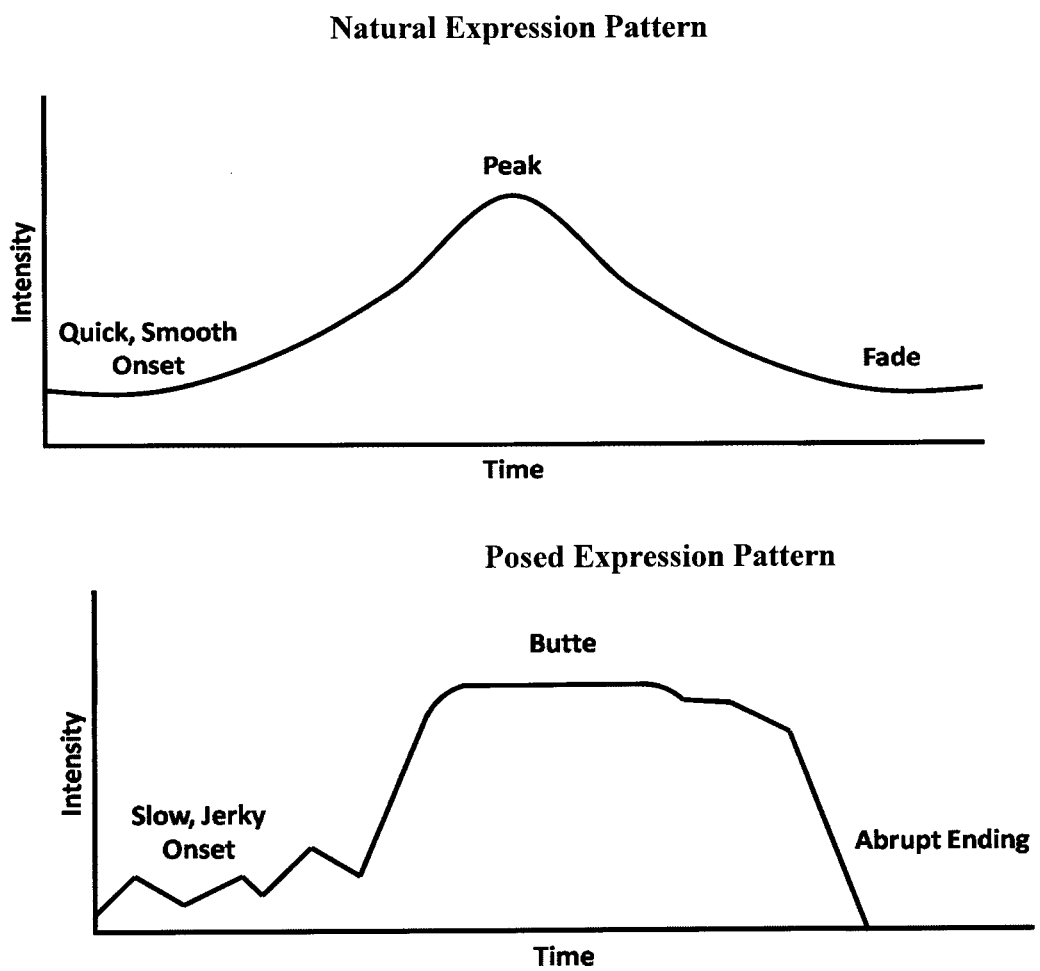
FIG. 15 illustrates two charts comparing natural vs. posed expressions according to one embodiment of the present disclosure.

Another embodiment can utilize frame-by-frame, split-second measurements to aid in the detection of possible instances of lying by taking into account a variety of patterns. Natural, involuntary expressions originate in the sub-cortical areas of the brain. These sub-cortically initiated facial expressions are characterized by synchronized, smooth, symmetrical, consistent and reflex-like facial muscle movements where volitional facial expressions tend to be less smooth. Thus an embodiment of this invention can account for whether a muscle activity has a natural onset (smooth and fast versus slow and jerky onsets for posed expressions), a peak and offset such that the emotion being shown flows on and off the face without the jerky onset, sudden ending rather than a natural fade or offset, or protracted peak—hereby dubbed a "butte"—that can mark an expression that may not be authentically felt. Likewise, software, as part of a system as described herein, may aid in noting expressions that are asymmetrical, such that one side of the face reveals the expression more than the other (in generally most cases except for contempt expressions, which are inherently unilateral) as an indication that the expression may be forced onto the face or otherwise contrived. Identifying odd timing, such that the expression arrives too early or late in conjunction with expressed statements and is as such out of synch, identifying mixed signals, where negative emotions accompany or are in the timing vicinity of a smile, noting when a surprise look or smile lasts more than expected, and detecting whether multiple action units peak simultaneously, or fail to do so, can be clues to an unnatural, posed expression. An example of a natural vs. posed flow for an action unit is shown in FIG. 15. As can be seen from FIG. 15, a natural expression typically exhibits a quick, smooth onset as the facial muscles relevant to a given action unit contract, extend, bulge, etc., a distinctive peak or apex where the intensity of the expression is strong, and an offset or fade whereby the action units subsides. In contrast, a faked, posed, voluntary, controlled or otherwise consciously mediated expression will more likely exhibit a slow, jerky onset, sustain itself as a "butte" with a distinct peak, and end quickly such as in the case of a "guillotine" smile that drops abruptly off the face.

One embodiment of the method of using non-verbal facial muscle activity or expressions to gain greater insights about an individual's personality type, behavioral tendencies, credibility, motivations and other such insights related to applications including but not limited to personnel hiring, career development, training, internet dating, and the analysis of people involved in law suits as witnesses or in actual or mock/shadow juries is to detect and note manually, in real-time if possible, the overall emotional look or expression that an individual might have at a given moment in response to a question, exposure to a stimulus, in enacting a scenario, etc. Thus, an outcome might be an analysis in which the conclusion is that somebody felt/looked "scared" when asked a given question. As an alternative to such an embodiment, either the person conducting the interview or else the person in question may work from a set of photographs, each showing a person exhibiting a given emotion, and selecting the one that best represents the person's overall emotional state, look or feeling that seems to have been evoked.

In another embodiment of the method, muscle activity contractions or other forms of movement might be observed and so noted, including the duration, intensity, and exact timing of such muscle activity or resulting, prevalent expressions. In this embodiment, the observation may be performed either manually by reviewing the video on a second-by-second basis to identify in terms of generalized movements and their meaning, what the person in question is feeling; or such analysis might be performed using a computerized system, as described in U.S. patent application Ser. No. 11/062,424. In such an embodiment, the outcome can be to note the take-away dominant emotion or emotions that a person is feeling, labeled, for example, as anger, fear, etc. or a combination thereof based, for instance, in concluding that since anger typically involves the contraction or tensing of muscles, and such was seen, then the person is exhibiting signs of anger. In contrast, cases where the face elongates, with raised eyebrows, mouth dropping open, etc., constitute, for example, signs of surprise.

In yet another embodiment of the method, muscle activity contractions or other forms of movement might again be observed and so noted, including the duration, intensity, and exact timing of such muscle activity or resulting expressions. In this embodiment, the observation may be again performed either manually by reviewing the video on a second-by-second basis to identify in terms of generalized movements and their meaning, what the person in question is feeling; or such analysis might be performed using a computerized system, as described in U.S. patent application Ser. No. 11/062,424. In this particular embodiment, facial coding based on the use of FACS or some other specific facial muscle activity coding system whereby a given facial muscle activity correlates to a specific unit of analysis, such for instance that the chin rising can be at once a sign, for example, of anger, disgust and sadness, can then in turn allow for the distinguishing of an array of emotional displays, with each, as an optional embodiment, being given a weighted percentage, leading, as another optional embodiment, to a range of scoring system outputs to identify the emotional displays that have been observed.

In yet another embodiment of the method, moreover, those displays can be construed to create a series of metric outputs, either directly related to the emotions shown, such as indicating the impact or intensity of emotions shown, and/or the appeal or valence of the emotions shown, etc. In a version of such an embodiment, analysis might proceed to correlate the emotional displays to determining or confirming the personality type of an individual, susceptibility to Behavioral Economic tendencies, degree of credibility, innate enthusiasm or engagement in a given topic, among other possibilities.

For any or all of the embodiments cited above, the method can be combined, correlated or otherwise linked to what people are saying, doing, hearing or seeing (in cases of visual stimuli, such as visuals aids in the courtroom) in relation to what kind of emoting accompanies the statements, behavior or exposure to stimuli. Moreover, the opportunity to systematically and scientifically observe, and quantify the emotional dimension of people for the purpose of adding emotional data non-invasively allows for getting beyond unreliable verbal statements or responses alone. As such, the method can possess several advantages, including but not limited to: (1) avoiding the risk that a person will, for instance, underreport consciously or subconsciously the degree to which they're not engaged by what the job entails, or that a negative trait like neuroticism applies to that person or over-report the degree to which a positive trait like agreeableness pertains to that person, for instance; (2) avoiding the additional expense and hassle of seeking to secure additional personality trait test results from people familiar with the person for the purpose of gaining greater reliability; (3) allowing for gathering emotional as opposed to rationally-oriented, cognitively filtered data as facial coding is geared to accessing and quantifying the emotional dimension; (4) in instances where the person is enacting a scenario, using facial coding to capture trait-related data allows for behavioral results as opposed to written or verbal input; and/or (5) providing an extra dimension to the analysis of witnesses or the reactions of mock juries, over and above what people will acknowledge or knowingly reveal.

For example, a company can use one embodiment of the method to better fill a sales position. Five people have applied, for example, and each of the applicants can be asked to take an IQ test, an unstructured interview with the director of sales, but also a structured interview format in which facial coding will be used to capture the EQ (emotional intelligence) and other dimensions of the job applicants to get a better read on their ability to handle the job. Because being an effective salesperson can involve qualities essential to success, such as but not limited to—1) resiliency (to accept hearing "no" from prospects and keep on going—2) optimism (to be upbeat and thus come across as confident and able to put the prospect at ease, and—3) empathy, so as to create a win/win scenario in negotiations—the format of the interview can consist of, for example, one or more questions related to each of those traits and one or more questions each related to each of the Big Five Factor model personality traits, for a total of 8 or more questions to be videotaped for review. In each case, the job applicant can be given 30 seconds, or some other reasonable period of time to respond, with both the audio and video to be reviewed and analyzed. In addition, a cold-call phone call scenario can be enacted by the job applicant, and videotaped for facial coding purposes, including, for example, one or more posed "objections" by the supposed receiver of the call, with the objections appearing on the display screen during the simulated cold call scenario. Afterwards, in accordance with this embodiment of the method, all 30-second question files and the 3-minute scenario can have the transcript analyzed, the video files facially coded, and the results tabulated. As a result of formulas involving the 10 emotional states shown earlier in the emotional profile, such as for instance sadness being incompatible with resiliency, or fear being indicative of neuroticism, for instance, statistical metrics can be produced indicating the job applicant's raw scores, comparisons against the norms for sales people, and the degree of fit for the job. For instance, previous research suggests that a good sales person will be extraverted, so that personality trait should be robust as identified by not only a written exam assessment of personality type, based on, for example, a 10-question written format rating system, but also as verified and explored through the facial coding findings.

In another embodiment, an internet dating service can have each new participant in the dating service take a self-assessment test or profile that will now include a video of their responses to select questions as well as in making a general introductory statement about themselves. Again, one or more questions can be asked to relate to each of the Big Five Factor model personality traits, with the general introductory statement potentially limited to, for example, 3 minutes, or some other suitable response time. These answers and the three minute introduction can then be reviewed in terms of facial coding results to identify the personality type of the individual, their overall level of engagement while making the introductory statement, the types of emotions they display during the video files, etc. That information can then available to members of the dating service who want to locate a person most suitable for them to date as a possible romantic partner. In a further embodiment of this example, a person who has then identified a limited range of people as potential partners may, for a fee, arrange for the service to ask additional questions related to values, attitudes, hobbies, etc., whereby the potential partner then records additional answers that will get videotaped, analyzed, and shared on a reporting basis with the dating service member who made the request. In that way, the dating service member can, for example, learn whether, for instance, the potential partner truly shares their enthusiasm for a given hobby, etc.

In another embodiment, a professional, such as a lawyer or psychiatrist can have a videotaped interview or deposition analyzed for the purposes of diagnosing their veracity, emotional state, types of motivations, etc. Such facial coding analysis alone or in conjunction with, for example, the transcribed comments can reveal what the witness, jury prospect, depressed client, etc., said, and how they felt while talking. Topics where there is a large degree of emoting, or emoting that might be incongruous with the statements made, can for example be flagged, suggesting that legal counsel or a psychologist might want to explore these aspects of the person's statement in greater depth because of incongruities between emotions felt and stated, the detection of potentially posed emotions, the absence or abundance of emotions related to a given topic, and so forth. In these cases, the video file may not have a set number of questions to be replied to, or timing elements. Instead, the video files can be captured for lengths of time ranging from, for example five minutes to an hour or more, with the possibility that in requesting facial coding analysis the lawyer or psychologist can identify certain time periods or topics from the transcript that should be explored, while omitting other videotaped material for reasons related to costs or turn-around time on the analysis. One advantage of securing facial coding analysis for a litigation attorney, for instance, may be that a videotaped deposition can be analyzed such that lines of inquiry that netted a high volume of emotional engagement, or negative emotions, for instance, such as fear, can indicate a place where greater scrutiny is called for because a key aspect of the case may have been inadvertently identified or else it may become evident that the person may not have revealed everything he or she knows about the matter subject to litigation, criminal investigation, etc. Meanwhile, for a mock jury facial coding analysis can prove of benefit in determining what lines of argumentation will resonate with, and convince, the actual jury in the case when presented in court.

Figure 16:
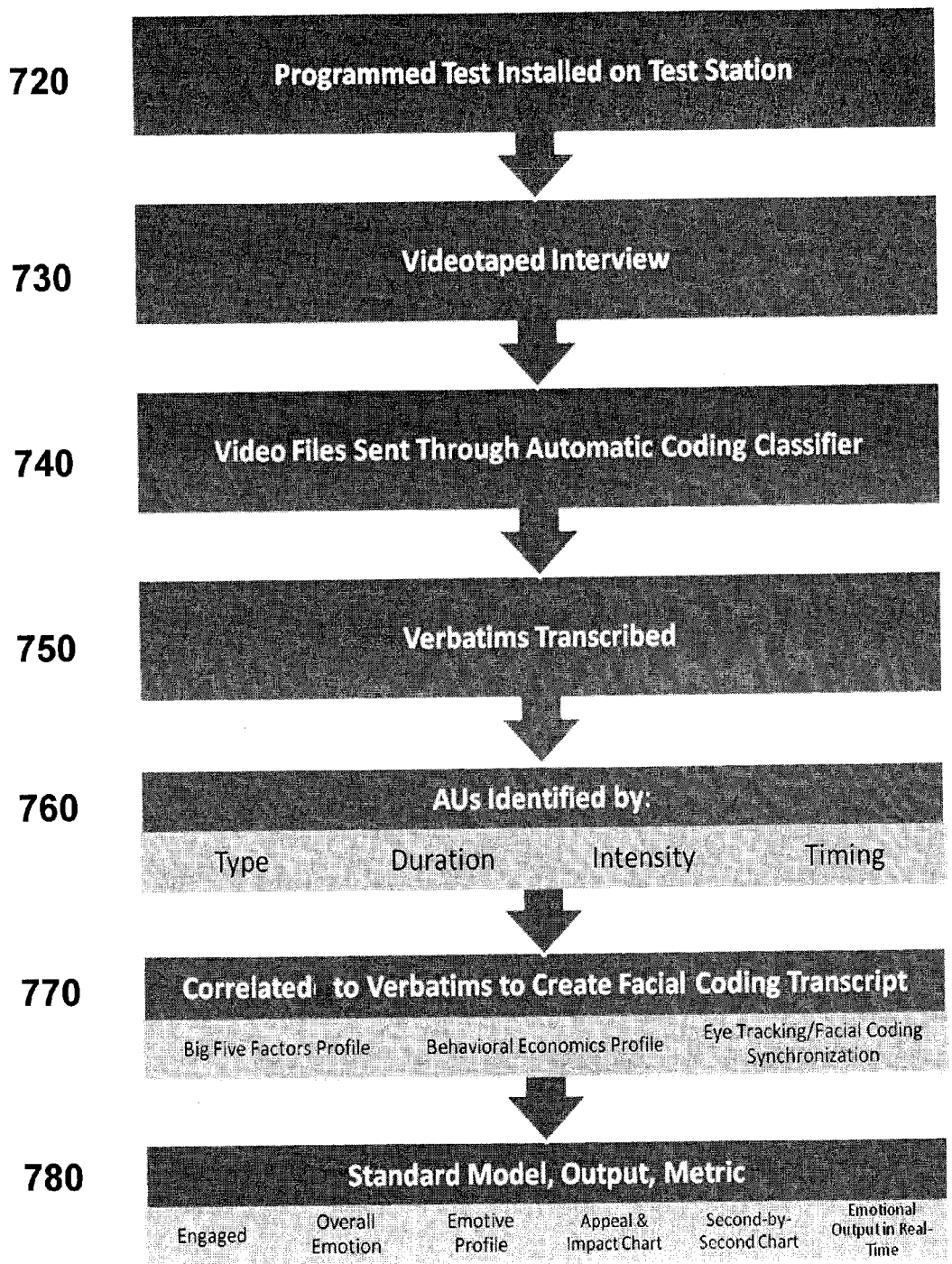
FIG. 16 is a process flow chart of the use of a system according to one embodiment of the present disclosure.

According to various embodiments of the present disclosure, a system can be implemented to at least partly automate the above-described methods. A flowchart of one embodiment of such a system is outlined in FIG. 16, and may include one or more of the following: programming the test station 720; interviewing the subject and recording the interview 730; automatically coding the video 740; transcribing the verbatims 750; identifying the AUs by type, duration, intensity, and/or timing 760, for example; correlating the AUs to verbatims to create a facial coding transcript 770 that may include a big five factor profile, behavioral economics profile, and/or eye tracking/facial coding synchronization, for example; and developing a statistical model, output, metric, etc. 780 that may include, for example, output relating to the extent to which the subject(s) is engaged, overall emotion of the subject(s), the emotive profile of the subject(s), appeal and impact charts for the subject(s), second by second charts, and/or emotional output in real time.

Figure 17:
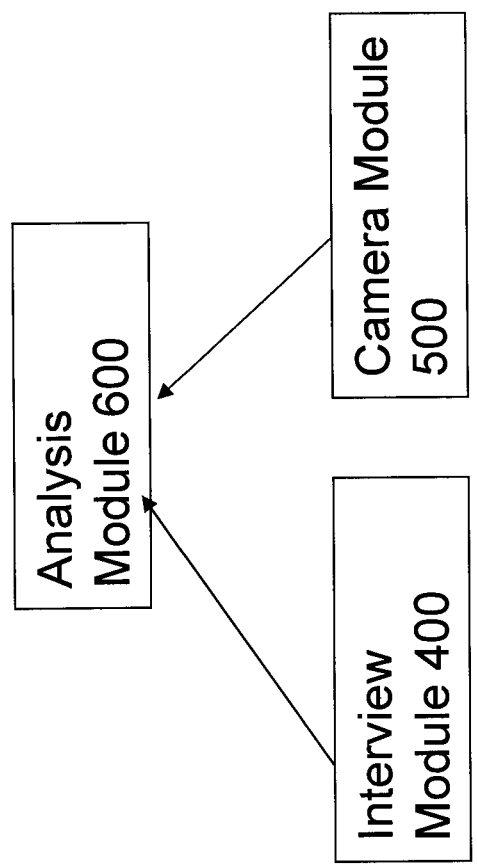
FIG. 17 is a schematic of an automated system according to one embodiment of the present disclosure.

FIG. 17 shows the components of one embodiment of an automated system for implementing the various methods of the present disclosure. The automated system may include one or more of an interview module 400, a camera module 500, and an analysis module 600.

Figure 18:
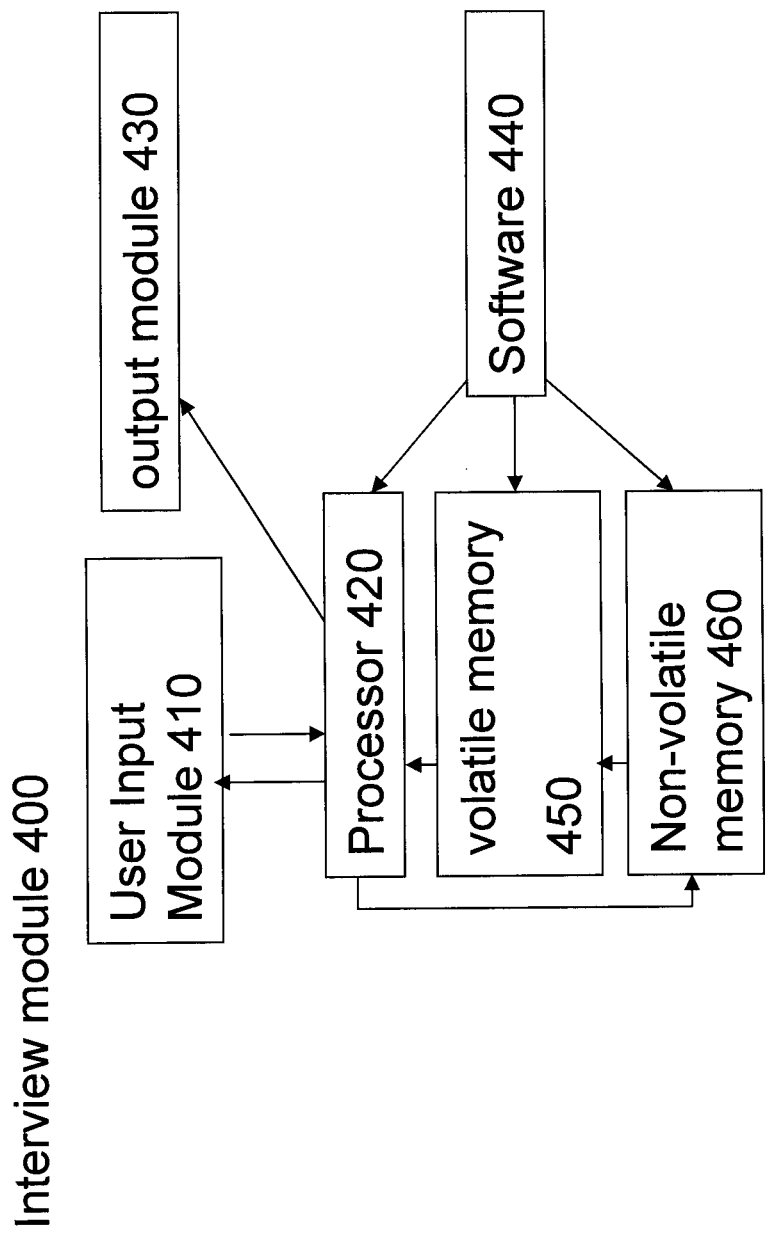
FIG. 18 is a schematic of an interview module of the automated system according to one embodiment of the present disclosure.

The interview module 400, as shown in FIG. 18 can be an interview computer system including a user input module 410, an output module 430, a processor 420, temporary volatile memory such as RAM 450, nonvolatile storage memory 460, and computer software 440. The user input module 410 can be a keyboard, a touch screen, vocal commands and responses, or any other method of interfacing with the computer system. The output module 430 could be a computer monitor, a projector, computer speakers, or any way of communicating to the subject of the interview. The processor 420 can be any general purpose or specialized computer processor such as those commercially available. The temporary volatile memory 450 can be any memory capable of or configured for storing code and/or executable computer instructions and data variables in memory. The nonvolatile storage memory 460 can be any memory capable of, or configured for storing computer instructions, either executable or non-executable, in object form or source code in non-volatile storage such as a hard drive, compact disc, or any other form of non-volatile storage. The computer software 440 can be specially developed for the purpose of interviewing the subject and/or capturing the video, or can be internet based, and delivered through third party browser applications.

Figure 19:
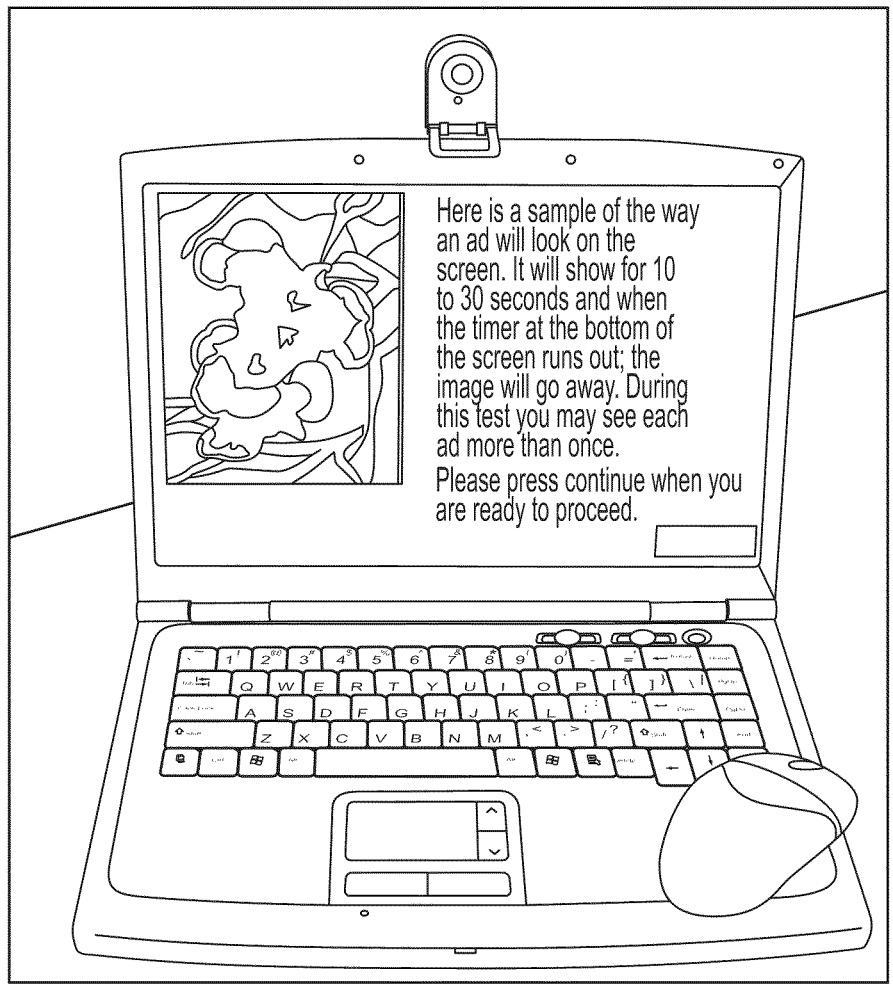
FIG. 19 is an example embodiment for collecting video according to one embodiment of the present disclosure.

A camera module 500 can be any device or hardware and software for capturing video of the subject during the stimulus and can include a camera, such as, but not limited to a web cam such as the setup depicted in FIG. 19, or a camera placed in surveillance mode, or any other suitable camera setup including a professional camera setup. In some embodiments, the video footage may allow for the viewing of at least two-thirds of the person's face, since some facial expressions are unilateral, not be so far away as to preclude seeing specific facial features with enough clarity to evaluate facial muscle activity, and not be obscured by the person hiding or otherwise obscuring their face with their hands, a coffee cup, etc. or by moving with such rapidity as to blur the video imagery. FIG. 19 shows how a web cam or video camera mounted on a personal computer, built into a personal computer, or elsewhere deployed in a room can capture video images of a person or persons as they are speaking, hearing, or seeing oral or written presentations of statements, or otherwise engaged in behavior, in order to capture their facial expressions in response to the stimuli, situation, or environment. The camera module 500 can be operably and/or electronically connected to the interview module and/or the analysis module 600.

In one embodiment, the process may begin by developing the question or questions, enactment scenarios, general statements, or other format that might be desirable for capturing video files in order to gauge the person in question. The format to be enacted can be made easier to enact on a standard, repeatable basis without operator error by using computer software to ensure that the format involves every element (question/scenario, etc.) in either a set order sequence or an order that is intentionally randomized. This software could first be programmed onto the test station computer via software 440. This can be a specialized application, an internet based application, or other suitable type of software. The questions or other elements of the format, including instructions, can either be shown on screen or verbalized using a played audio file via output module 430 to deliver each step in the process of gaining data from the person in question. Typically, a suitable response interval can be set for a duration of 30 seconds to 2 minutes in length. A scenario, for example, can suitably run for 2 to 5 minutes, or any other desirable amount of time.

Once the interview module and the camera module are setup, then the videotaped interview or format for gathering input can commence. The interview session may be recorded by the camera module 500 which can be setup to ensure high quality images of the participant's facial expression as obtained throughout the session. The person can be instructed, for example, to (i) look into the camera (ii) avoid any extreme or radical head movement during the session and (iii) keep from touching their face during the session. A reasonably close up filming can be used, including one in which the person's face is at least ¾ths visible as opposed to a profile filming positioning. Both the oral statements (audio) and the facial expressions (video) can be captured by the camera for the purposes of subsequent review, or the video files alone can be solely captured for the purposes of the analysis to be performed.

Figure 20:
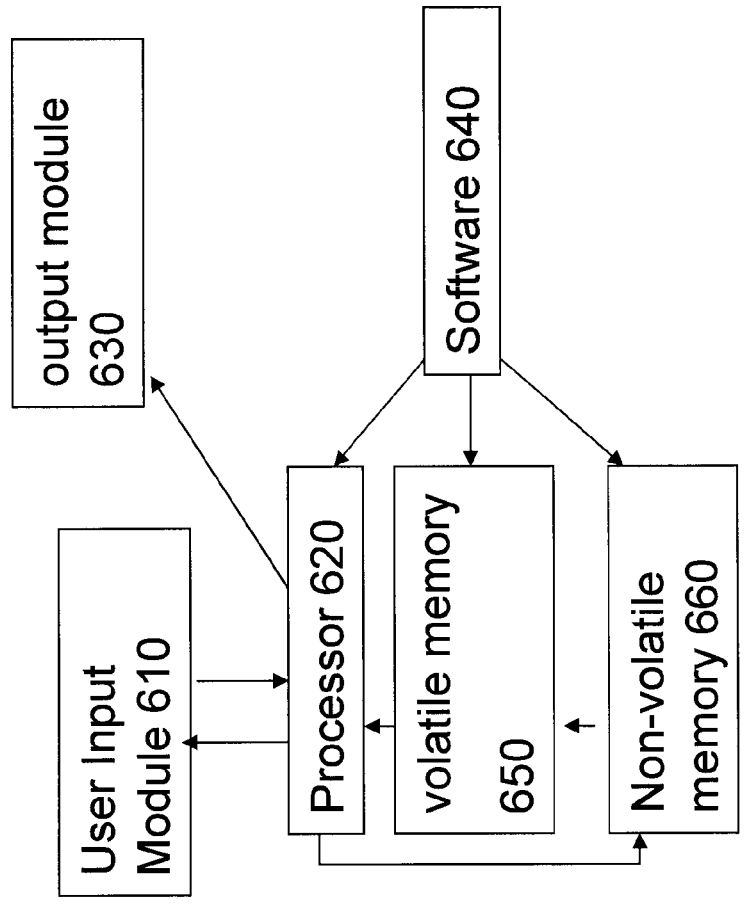
FIG. 20 is a schematic of an analysis module of the automated system according to one embodiment of the present disclosure.
Figure 21:
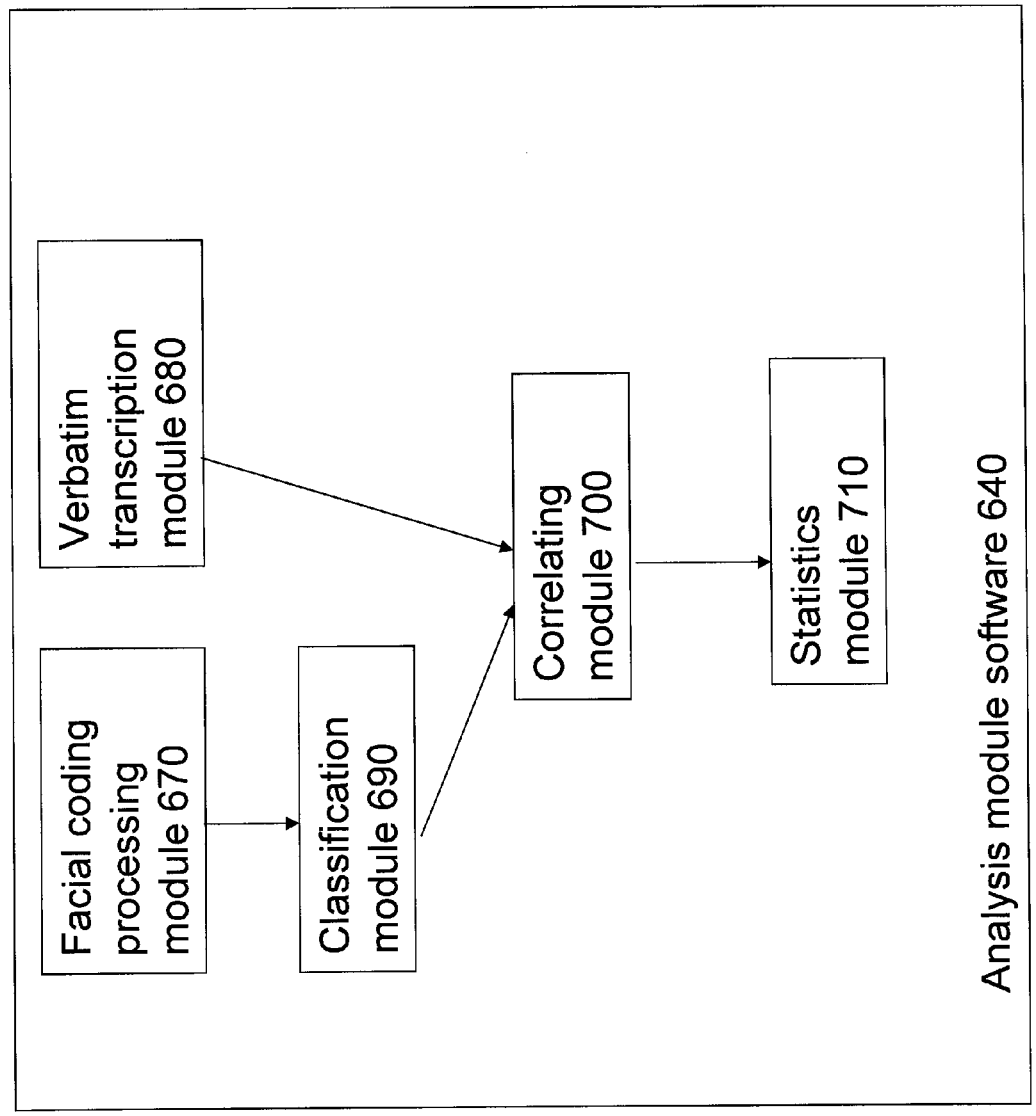
FIG. 21 is a schematic of analysis module software according to one embodiment of the present disclosure.

After the interview is over, the data collected can be sent to the analysis module 600. The analysis module, as shown in FIG. 20, can be a computer system including a user input module 610, an output module 630, a processor 620, temporary volatile memory 650 such as RAM, nonvolatile storage memory 660, and computer software 640. The user input module 610 can be a keyboard, a touch screen, vocal commands and responses, or any other method of interfacing with the computer system. The output module 630 could be a computer monitor, a projector, computer speakers, or any way of communicating to the subject of the interview. The processor 620 can be any general purpose computer processor such as those commercially available. The temporary volatile memory 650 can be any memory capable of, or configured for storing code and/or executable computer instructions and data variables in memory. The nonvolatile storage memory 660 can be any memory capable of, or configured for storing computer instructions, either executable or non-executable, in object form or source code in non-volatile storage such as a hard drive, compact disc, or any other form of non-volatile storage. The computer software 640 can be specially developed for the purpose of analyzing the data, or can be based on third party applications. The computer software as shown in FIG. 21 can include one or more of a facial coding processing module 670, a verbatim transcription module 680, a classification module 690, a correlating module 700, and a statistical module 710.

The facial coding processing module 670 that could be utilized herein can be hardware and/or software that is configured to read the facial muscle activity, AUs, and/or general expressions of people based on the repetitious refinement of algorithms trained to detect the action units that correspond to emotions in FACS or through any other method of analyzing and scoring facial expressions. To do so, the processing module can take into account the movement of facial muscles in terms of a changed alignment of facial features, plotting the distance between the nose and mouth, for instance, such that when an uplifted mouth may, for example, signal disgust, the distance between the nose and mouth is reduced and the presence of an AU 10, disgust display, is documented, including potentially the duration of the expression, its intensity, and the specific time element that denotes when the expression hit its emotional high-point or peak. Likewise, the processing module can be configured to do all of the various computations described in the preceding paragraphs.

The facial coding processing module 670 may include software modules, such as but not limited to, software under development by ReallaeR, for instance, where FACS is concerned, or if for general facial muscle activity, perhaps defined as "motion units," then as available from VicarVision. A range of other coding system for facial muscle activity might likewise be in various stages of development from universities such as the University of California, San Diego (UCSD), MIT, Carnegie Mellon, the University of Pittsburgh, alone or in collaboration between sets of academics and/or their business or governmental sponsors. Generally, the processing module 670 may involve the assistance of a computerized program with software that reads a person or group's facial expressions automatically. Over time, the algorithms on which the analysis is based will derive results such that a database can be built up to reflect which types of emotional responses fit various outcomes, like greater likelihood to be a good romantic partner, a productive employee, a manager or executive highly skilled at exhibiting emotional intelligence in interacting with others, etc.

With the advent of such systems as described herein, it might also be more feasible to serve target markets like doctors and psychologists aiming to aid those who struggle with alcohol addiction, depression, and other forms of psychopathology or in police detection work, man-machine communication, healthcare, security, education, remote surveillance, and telecommunications. Additionally, video files can be reviewed and analyzed for credibility, emotive displays, etc., as submitted by individuals through social internet networking sites where people want to gain credible assessments of others or of situations and behaviors. Further, such systems as described herein can facilitate the task of facial action detection of spontaneous facial expressions in real-time. Such systems can recognize which muscles are moved, and the dynamics of the movement. Machine learning methods, like support vector machines and AdaBoost, for example, can be used to aid texture-based image representations. Machine learning methods applied to the related problem of classifying expressions of basic emotions can likewise involve linear discriminant analysis, feature selection techniques, Gabor filters, and other such tools as may be developed and/or prove relevant to the process. Image-based presentations that account for image texture can also be used. Such software can also take into account speech related mouth and face movements, and in-plane and in-depth movements by the subject being coded. Moreover, such software could be adept in considering how blends of multiple action units happening simultaneously or in overlapping timeframes cause a given AU to adopt a somewhat different appearance.

A manual or automatic transcription of the verbatims from the answers given during the interview can be created by the verbatim transcription module 680. The analysis module can either automatically create the transcript using speech recognition software, or the manual transcription can be entered into the module via the user input module, or sent to, or otherwise transferred to the analysis module.

The automated software's classification module 690 can then be deployed to identify one or more of the type, duration, intensity and specific timeframe for each AU shown by a given person. The captured video can for facial coding purposes be analyzed on a second-by-second basis, e.g., 30 frames per second, to identify the action units or other types of facial expressions that will become the basis for the analysis. Those action units can be accumulated per person, or group, in relation to a given question, statement, stimulus or scenario being enacted. Those results can, if desirable, then be correlated according to the methods described above to, for example, the completed verbatim transcription by the correlation module 700.

The correlation module 700 can be any automated, or computer assisted means of correlating the results of the classifier 690 with the verbatim transcriptions. The correlation could also be done manually.

The statistical module 710 can then work from pre-established algorithms, as described above, to derive the statistical output, such as that related to engagement, overall emotion (including by topic), emotional profile, appeal and impact chart, second-by-second chart, and/or emotional displays in real-time, for example. Moreover, in some embodiments, this step can include deriving a Big Five Factor model personality type data, a Behavioral Economics profile, and/or eye tracking and facial coding synchronized results. Moreover, in reviewing the linkages between verbatims and facial coding data, and even the nature or characteristics of the emotional displays, examination can be done to identify the topics that elicited what types of emotion, where emotion was absent, when the emotion seemed more posed or genuinely felt, where veracity is suspect, and the like. The output may then be displayed on by the output module 630, or sent to any other system or printed, or otherwise delivered in a suitable manner.

In the foregoing description, various embodiments of the disclosure have been presented for the purpose of illustration and description. They are not intended to be exhaustive or to limit the disclosure to the precise form disclosed. Obvious modifications or variations are possible in light of the above teachings. The embodiments were chosen and described to provide the best illustration of the principals of the disclosure and its practical application, and to enable one of ordinary skill in the art to utilize the various embodiments with various modifications as are suited to the particular use contemplated. All such modifications and variations are within the scope of the disclosure as determined by the appended claims when interpreted in accordance with the breadth they are fairly, legally, and equitably entitled.

I claim:

1. A method of assessing an individual through facial muscle activity and expressions, the method comprising:
   (a) receiving a recording stored on a computer-readable medium of an individual's response to a stimulus, the recording including a non-verbal response comprising facial expressions of the individual;
   (b) accessing the computer-readable medium for detecting and recording expressional repositioning of each of a plurality of selected facial features by conducting a computerized comparison of the facial position of each selected facial feature through sequential facial images;
   (c) coding contemporaneously detected and recorded expressional repositionings to at least one of an action unit, a combination of action units, or at least one emotion; and
   (d) analyzing the at least one of an action unit, a combination of action units, or at least one emotion to assess one or more characteristics of the individual to develop a profile of the individual's personality in relation to the objective for which the individual is being assessed, wherein analyzing the at least one of an action unit, a combination of action units, or at least one emotion comprises:
identifying moments of the recording that elicited emotion based on the at least one of an action unit, a combination of action units, or at least one emotion; and
developing the profile of the individual's personality based on a percentage of positive versus negative emotions and the specific emotions shown during the stimulus.

2. The method of claim 1, wherein the received recording comprises a verbal response to the stimulus, and wherein analyzing the at least one of an action unit, a combination of action units, or at least one emotion comprises assessing the at least one emotion against a portion of the individual's verbal response to assess one or more characteristics of the individual with respect to the individual's verbal response.

3. The method of claim 2, wherein the verbal responses are categorized by topic.

4. The method of claim 2, further comprising creating a transcript of at least a portion of the individual's verbal response, and analyzing the at least one of an action unit, a combination of action units, or at least one emotion comprises one or more of:
identifying places in the transcript of emotional response;
identifying the valence of the emotions for places in the transcript;
identifying one or more emotions that are most predominant with respect to at least portions of the transcript; and
identifying discrepancies between the verbal response and emotive response of the individual.

5. The method of claim 1, wherein detecting and recording facial expressional repositioning of each of a plurality of selected facial features comprises recording the timing of the detected repositioning for peak emoting and real-time duration.

6. The method of claim 1, wherein coding contemporaneously detected and recorded expressional repositionings comprises automatically coding a single action unit or combination of action units to at least one corresponding emotion by percentage or type.

7. The method of claim 1, wherein coding contemporaneously detected and recorded expressional repositionings comprises coding a single action unit or combination of action units to a weighted value.

8. The method of claim 1, wherein analyzing the at least one of an action unit, a combination of action units, or at least one emotion comprises determining whether the individual's emotional response is predominantly positive, neutral, or negative.

9. The method of claim 1, wherein analyzing the at least one of an action unit, a combination of action units, or at least one emotion comprises quantifying the volume of emotion to determine the degree to which the individual is engaged or enthusiastic.

10. The method of claim 1, wherein analyzing the at least one of an action unit, a combination of action units, or at least one emotion comprises analyzing the degree of intensity for each action unit or combination of action units to determine the degree to which the individual is engaged or enthusiastic.

11. The method of claim 1, wherein analyzing the at least one of an action unit, a combination of action units, or at least one emotion comprises corresponding the at least one of an action unit, a combination of action units, or at least one emotion by stimulus type to relate emotional response data for the individual to a formula for determining the degree to which the individual fits one or more of the Big Five Factor model personality traits.

12. The method of claim 1, wherein analyzing the at least one of an action unit, a combination of action units, or at least one emotion comprises corresponding the at least one of an action unit, a combination of action units, or at least one emotion by stimulus type for determining the degree to which the individual is susceptible to one or more of the biases identified as part of Behavioral Economics.

13. The method of claim 1, wherein the stimulus comprises one or more of questions, statements, or scenarios.

14. The method of claim 13, wherein the objective the individual is being assessed for is the individual's suitability for a job position or task related to a job.

15. The method of claim 13, wherein the objective the individual is being assessed for is to determine potential romantic partners.

16. The method of claim 13, wherein the objective the individual is being assessed for is to ascertain one or more of emotional responses, potential veracity, personality type, and levels of enthusiasm for legal applications.

17. The method of claim 1, further comprising linking eye tracking data from the recording with the at least one of an action unit, a combination of action units, or at least one emotion.

18. The method of claim 1, wherein coding contemporaneously detected and recorded expressional repositionings to at least one of an action unit, a combination of action units, or at least one emotion comprises coding contemporaneously detected and recorded expressional repositionings to a plurality of weighted emotions.

19. A non-transitory machine-readable medium including instructions that, when executed by a machine, cause the machine to perform, operations comprising:
(a) receiving a recording stored on a computer-readable medium of an individual's response to a stimulus, the recording including a non-verbal response comprising facial expressions of the individual;
(b) accessing the computer-readable medium for automatically detecting and recording expressional repositioning of each of a plurality of selected facial features by conducting a computerized comparison of the facial position of each selected facial feature through sequential facial images;
(c) automatically coding contemporaneously detected and recorded expressional repositionings to at least one of an action unit, a combination of action units, or at least one emotion; and
(d) analyzing the at least one of an action unit, a combination of action units, or at least one emotion to assess one or more characteristics of the individual to develop a profile of the individual's personality in relation to the objective for which the individual is being assessed, wherein analyzing the at least one of an action unit, a combination of action units, or at least one emotion comprises:
identifying moments of the recording that elicited emotion based on the at least one of an action unit, a combination of action units, or at least one emotion; and
developing the profile of the individual's personality based on a percentage of positive versus negative emotions and the specific emotions shown during the stimulus.

20. The machine-readable medium of claim 19, wherein the received recording comprises a verbal response to the stimulus, and wherein analyzing the at least one of an action unit, a combination of action units, or at least one emotion comprises assessing the at least one emotion against a portion of the individual's verbal response to assess one or more characteristics of the individual with respect to the individual's verbal response.

21. The machine-readable medium of claim 20, further comprising instructions causing the machine to perform operations comprising creating a transcript of at least a portion of the individual's verbal response, and analyzing the at least one of an action unit, a combination of action units, or at least one emotion comprises one or more of:

identifying places in the transcript of emotional response;
identifying the valence of the emotions for places in the transcript;
identifying one or more emotions that are most predominant with respect to at least portions of the transcript; and
identifying discrepancies between the verbal response and emotive response of the individual.

22. The machine-readable medium of claim 19, wherein coding contemporaneously detected and recorded expressional repositionings comprises automatically coding a single action unit or combination of action units to at least one corresponding emotion by percentage or type.

23. The machine-readable medium of claim 19, wherein analyzing the at least one of an action unit, a combination of action units, or at least one emotion comprises determining whether the individual's emotional response is predominantly positive, neutral, or negative.

24. The machine-readable medium of claim 19, wherein analyzing the at least one of an action unit, a combination of action units, or at least one emotion comprises quantifying the volume of emotion to determine the degree to which the individual is engaged or enthusiastic.

25. The machine-readable medium of claim 19, wherein analyzing the at least one of an action unit, a combination of action units, or at least one emotion comprises analyzing the degree of intensity for each action unit or combination of action units to determine the degree to which the individual is engaged or enthusiastic.

26. The machine-readable medium of claim 19, wherein analyzing the at least one of an action unit, a combination of action units, or at least one emotion comprises corresponding the at least one of an action unit, a combination of action units, or at least one emotion by stimulus type to relate emotional response data for the individual to a formula for determining the degree to which the individual fits one or more of the Big Five Factor model personality traits.

27. The machine-readable medium of claim 19, wherein analyzing the at least one of an action unit, a combination of action units, or at least one emotion comprises corresponding the at least one of an action unit, a combination of action units, or at least one emotion by stimulus type for determining the degree to which the individual is susceptible to one or more of the biases identified as part of Behavioral Economics.

28. The machine-readable medium of claim 19, further comprising instructions causing the machine to perform operations comprising linking eye tracking data from the recording with the at least one of an action unit, a combination of action units, or at least one emotion.

* * * * *